(12) United States Patent
Hanson et al.

(10) Patent No.: US 11,571,563 B2
(45) Date of Patent: Feb. 7, 2023

(54) ELECTRICALLY CONDUCTIVE EAR TIPS

(71) Applicant: Bose Corporation, Framingham, MA (US)

(72) Inventors: Caitlin Hanson, Tyngsboro, MA (US); Shawn J. Prevoir, Northborough, MA (US)

(73) Assignee: Bose Corporation, Framingham, MA (US)

( * ) Notice: Subject to any disclaimer, the term of this patent is extended or adjusted under 35 U.S.C. 154(b) by 389 days.

(21) Appl. No.: 16/567,796

(22) Filed: Sep. 11, 2019

(65) Prior Publication Data
US 2021/0069490 A1 Mar. 11, 2021

(51) Int. Cl.
| *A61N 1/04* | (2006.01) |
| *A61N 1/36* | (2006.01) |
| *A61L 31/02* | (2006.01) |
| *A61L 31/06* | (2006.01) |
| *A61L 31/14* | (2006.01) |
| *H04R 1/10* | (2006.01) |

(52) U.S. Cl.
CPC .......... *A61N 1/0496* (2013.01); *A61L 31/028* (2013.01); *A61L 31/06* (2013.01); *A61L 31/145* (2013.01); *A61N 1/36036* (2017.08); *H04R 1/1016* (2013.01); *H04R 1/1058* (2013.01); *A61N 1/0456* (2013.01); *A61N 1/36014* (2013.01)

(58) Field of Classification Search
None
See application file for complete search history.

(56) References Cited

U.S. PATENT DOCUMENTS

| 8,249,287 | B2 | 8/2012 | Silvestri et al. |
| 10,057,675 | B2 | 8/2018 | Mankodi et al. |
| 2005/0215727 | A1 | 9/2005 | Feldstein et al. |
| 2011/0007929 | A1 | 1/2011 | Rabu et al. |
| 2017/0360994 | A1* | 12/2017 | Havenstrite .......... A61L 29/145 |
| 2017/0361094 | A1* | 12/2017 | Cartledge ............ A61N 1/0456 |
| 2018/0021564 | A1* | 1/2018 | Goodall ............... A61N 1/0526 600/379 |
| 2018/0235540 | A1 | 8/2018 | Kirszenblat et al. |
| 2018/0295439 | A1 | 10/2018 | Garrett |
| 2019/0053756 | A1 | 2/2019 | Ayers et al. |

FOREIGN PATENT DOCUMENTS

| WO | 2010032112 A2 | 3/2010 |
| WO | 2018071630 A1 | 4/2018 |
| WO | 2019046757 A1 | 3/2019 |

OTHER PUBLICATIONS

International Search Report and Written Opinion dated Nov. 21, 2020 for PCT/US2020/050046.

(Continued)

*Primary Examiner* — Michael W Kahelin
(74) *Attorney, Agent, or Firm* — Bose Corporation

(57) ABSTRACT

An earpiece includes an earbud that supports at least one electrode, and an ear tip that includes a hydrogel. The ear tip is configured to be coupled to the earbud such that the hydrogel overlies the at least one electrode and such that the hydrogel is disposed between the at least one electrode and the user's skin when the earpiece is worn.

12 Claims, 24 Drawing Sheets

(56) References Cited

OTHER PUBLICATIONS

Kidmose, Preben, et al. "A Studt of Evoked Potentials From Ear-EEG". IEEE Transactions on Biomedical Engineering, vol. 60, No. 10, Oct. 2013.
Goverdovsky, Valentin, et al., "Hearables: Multimodal physiological in-ear sensing", Scientific Reports, received Jan. 10, 2017.
Kappel, Simon L., et al., "Dry-Contact Electrode Ear-EEG", IEEE 2018.
Looney, David, et al., "The In-the-Ear Recording Concept", IEEE Pulse 33, Dec. 11, 2012.

* cited by examiner

ELECTRICALLY CONDUCTIVE EAR TIPS

BACKGROUND

This disclosure relates to electrically conductive ear tips.

SUMMARY

All examples and features mentioned below can be combined in any technically possible way.

In one aspect, an earpiece includes an earbud that supports at least one electrode, and an ear tip that includes a hydrogel. The ear tip is configured to be coupled to the earbud such that the hydrogel overlies the at least one electrode and such that the hydrogel is disposed between the at least one electrode and the user's skin when the earpiece is worn.

Implementations may include one or more of the following features, or any combination thereof.

In some implementations, the hydrogel includes Poly(N-isopropylacrylamide).

In certain implementations, the hydrogel is hydrated with an electrically conductive liquid In some cases, the electrically conductive liquid includes salt water.

In certain cases, the hydrogel includes a strengthening additive (e.g., cellulose nanocrystals).

In some examples, the hydrogel includes 1% to 10% of the strengthening additive by weight.

In certain examples, the hydrogel includes an anti-microbial additive (e.g., silver phosphate glass).

In some implementations, the hydrogel comprises 0.1% to 1% of anti-microbial additive by weight.

Another aspect features an earpiece that includes an earbud that supports at least one electrode, and an ear tip. The ear tip includes a body having a deformable outer wall. An electrically conductive element is arranged on an outer surface of the deformable outer wall and is configured to be electrically coupled to the at least one electrode when the ear tip is mechanically coupled to the earbud. A coating overlies the conductive element such that the coating is disposed between the conductive element and a user's skin when the earpiece is worn.

Implementations may include one of the above and/or below features, or any combination thereof.

In some implementations, the coating includes hydrogel (e.g., Poly(N-isopropylacrylamide)).

In certain implementations, the hydrogel is hydrated with an electrically conductive liquid.

In some cases, the coating includes an ionomer (e.g., a hygroscopic polymer).

In certain cases, the ionomer is selected from the group consisting of: a sulfonated tetrafluoroethylene based fluoropolymer-copolymer; a sulfonated poly(styrene-b-isobutylene-b-styrene) (S-SIBS), and a sulfonated polystyrene-b-poly(ethylene-r-butylene)-b-polystyrene (S-SEBS).

In some examples, the coating is deposited on the conductive element via chemical vapor deposition.

In certain examples, the coating has micropores that trap moisture.

In some implementations, the coating is hygroscopic.

In certain implementations, the body has first and second ends and an inner wall extending between the first and second ends. The deformable outer wall is connected to the inner wall of the body at the first end and tapers away from the inner wall toward the second end. The inner wall includes at least one conductive lead configured to electrically connect with the electrically conductive element when the outer wall is deformed toward the inner wall.

In some cases, the body has first and second ends and an inner wall extending between the first and second ends. The deformable outer wall is connected to the inner wall of the body at the first end and tapers away from the inner wall toward the second end. The electrically conductive element extends along the outer surface of the deformable outer wall and an inner surface of the inner wall.

Another aspect provides an earpiece that includes an earbud that supports at least one electrode, and an ear tip. The ear tip includes a body having a deformable outer wall, and an electrically conductive element that is arranged on an outer surface of the deformable outer wall and is configured to be electrically coupled to the at least one electrode when the ear tip is mechanically coupled to the earbud. The electrically conductive element includes a plurality of microstructures that extend outwardly from an outer surface of the electrically conductive element.

Implementations may include one of the above and/or below features, or any combination thereof.

In some implementations, the electrically conductive material includes a thermoplastic elastomer that defines the microstructures.

In certain implementations, the earpiece includes an electrically conductive coating on the outer surface of the electrically conductive element.

In some cases, the electrically conductive coating includes a silver-silver chloride (Ag/AgCl) ink.

In certain cases, the microstructures include micropillars.

In some examples, the body is formed of silicone, polyurethane, polydimethylsiloxane, polynorbornene, thermoplastic elastomer, and/or fluoroelastomer.

In certain examples, the deformable outer wall is generally frustoconical in shape.

In some implementations, the body has first and second ends and an inner wall extending between the first and second ends. The deformable outer wall is connected to the inner wall of the body at the first end and tapers away from the inner wall toward the second end. The electrically conductive element extends along the outer surface of the deformable outer wall and an inner surface of the inner wall.

Yet another aspect features an ear worn device for delivering vagus nerve stimulation therapy. The device includes first and second contacts and a coupling member that mechanically couples the first and second contact. The first contact is configured to rest against a cymba concha of a user's ear and includes a first electrode and a first cover layer that overlies the first electrode such that the first cover layer is disposed between the first electrode and the user's skin when worn. The second contact is configured to rest against a tragus of the user's ear and includes a second electrode and a second cover layer that overlies the second electrode such that the second cover layer is disposed between the second electrode and the user's skin when worn.

Implementations may include one of the above and/or below features, or any combination thereof.

In some implementations, the coupling member is configured to wrap at least partially around a user's ear.

In certain implementations, the first and/or second cover layer includes a hydrogel.

In some cases, the hydrogel is hydrated with an electrically conductive liquid.

In certain cases, the hydrogel includes Poly(N-isopropylacrylamide).

In some examples, the first and/or second cover layer includes an ionomer.

In certain examples, the ionomer includes a hygroscopic polymer.

In some implementations, the ionomer is selected from the group consisting of: a sulfonated tetrafluoroethylene based fluoropolymer-copolymer; a sulfonated poly(styrene-b-isobutylene-b-styrene) (S-SIBS); and a sulfonated polystyrene-b-poly(ethylene-r-butylene)-b-polystyrene (S-SEBS).

Another aspect provides eyeglasses. The eyeglasses include a frame having a frontal region, and a pair of temple pieces extending from the frontal region. At least one electrode is supported on at least one of the temple pieces. A cover layer overlies the at least one electrode such that the cover layer is disposed between the at least one electrode and a user's skin when the eyeglasses are worn.

Implementations may include one of the above and/or below features, or any combination thereof.

In some implementations, the cover layer includes a hydrogel.

In certain implementations, the hydrogel is hydrated with an electrically conductive liquid.

In some cases, the cover layer includes an ionomer.

In certain cases, the cover layer is a coating bonded to an outer surface of the at least one electrode.

In some examples, the cover layer is a removable tip.

In certain examples, the removable tip is formed of a hydrogel.

In some implementations, at least one electro-acoustic transducer is supported by at least one of the temple pieces.

According to another aspect, an audio device includes an audio device body that is configured to be carried on an ear pinna and/or a head at or proximate an ear root region where the pinna meets the head. An acoustic module is coupled to the audio device body. An electro-acoustic transducer is supported by the acoustic module. An arm is coupled to the body. One or more electrodes are supported on one or more of the audio device body, the acoustic module, and the arm.

Implementations may include one of the above and/or below features, or any combination thereof.

In some implementations, a cover layer overlies the at least one electrode such that the cover layer is disposed between the at least one electrode and a user's skin when the audio device is worn.

In certain implementations, the cover layer includes a hydrogel.

In some cases, the hydrogel is hydrated with an electrically conductive liquid.

In certain cases, the cover layer includes an ionomer.

In some examples, the arm is movable relative to the body.

Figure 1A:
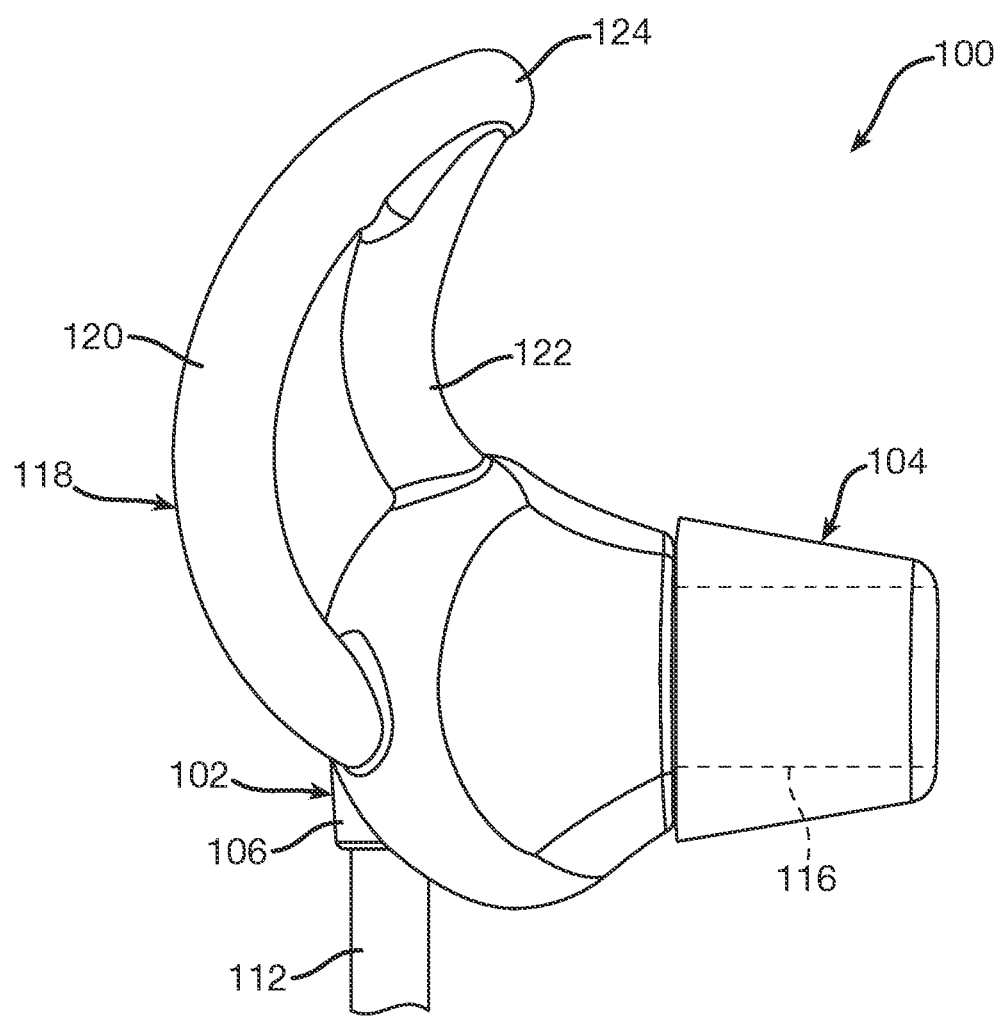
FIG. 1A is a front view of an example earpiece.
Figure 1B:
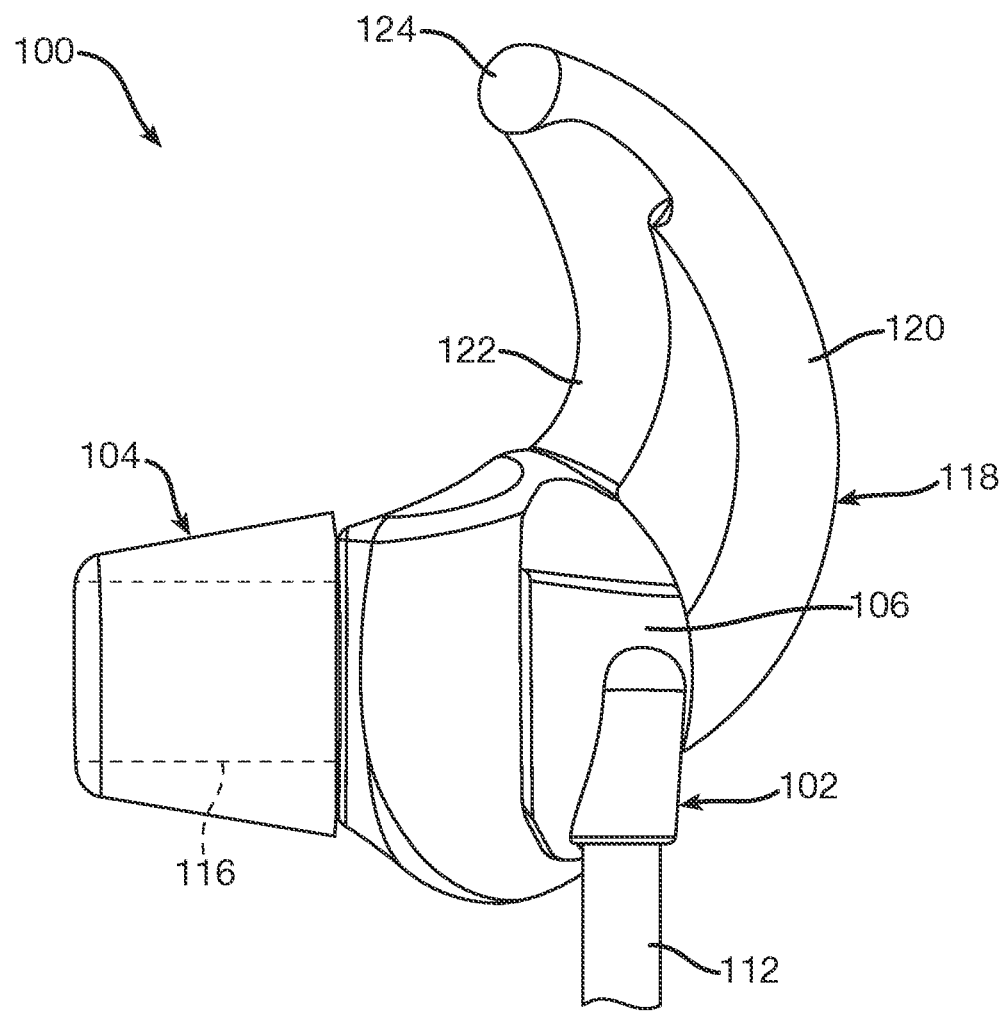
FIG. 1B is an exploded front view of the earpiece of FIG. 1A.
Figure 1C:
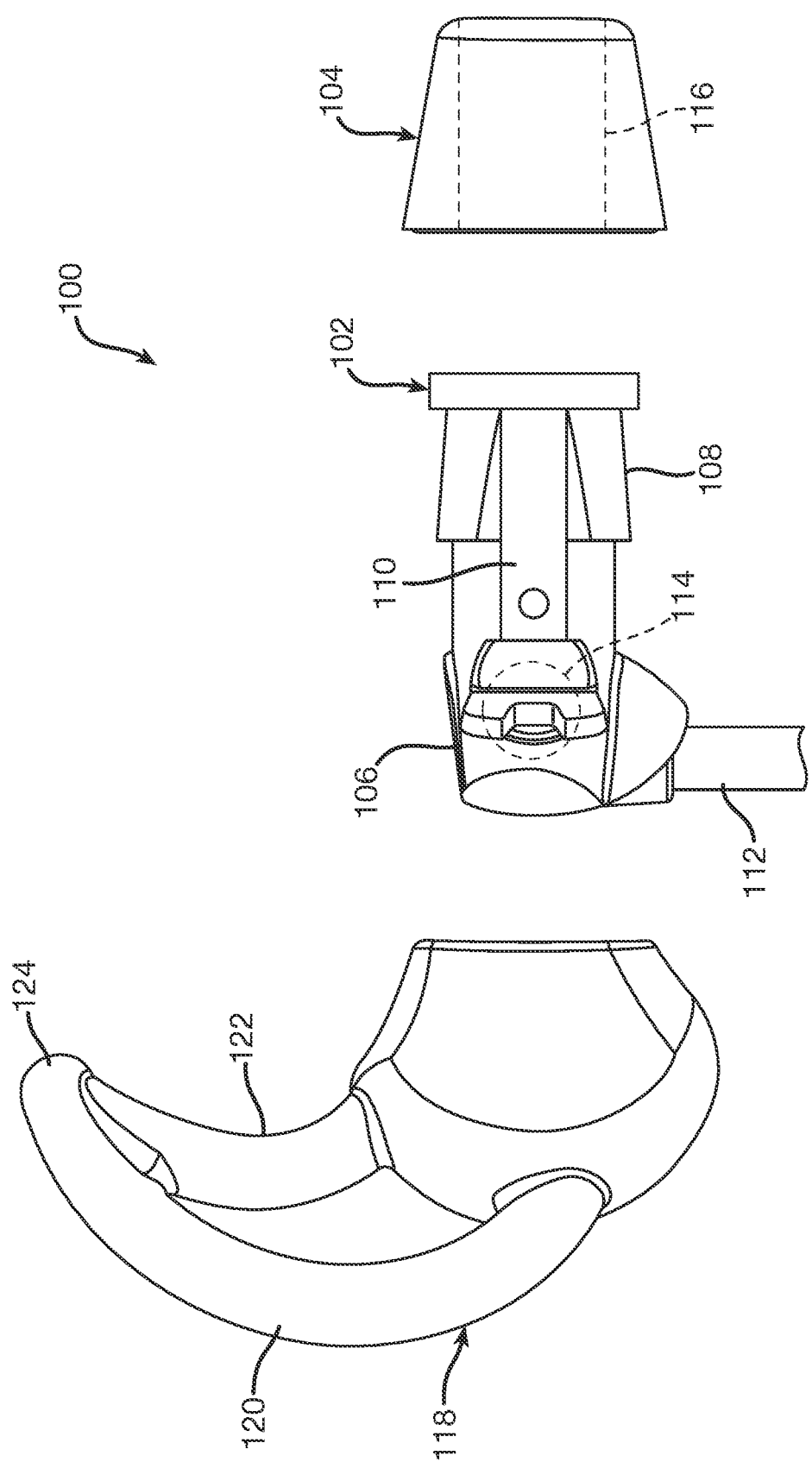
FIG. 1C is a rear view of the example earpiece of FIG. 1A.
Figure 1D:
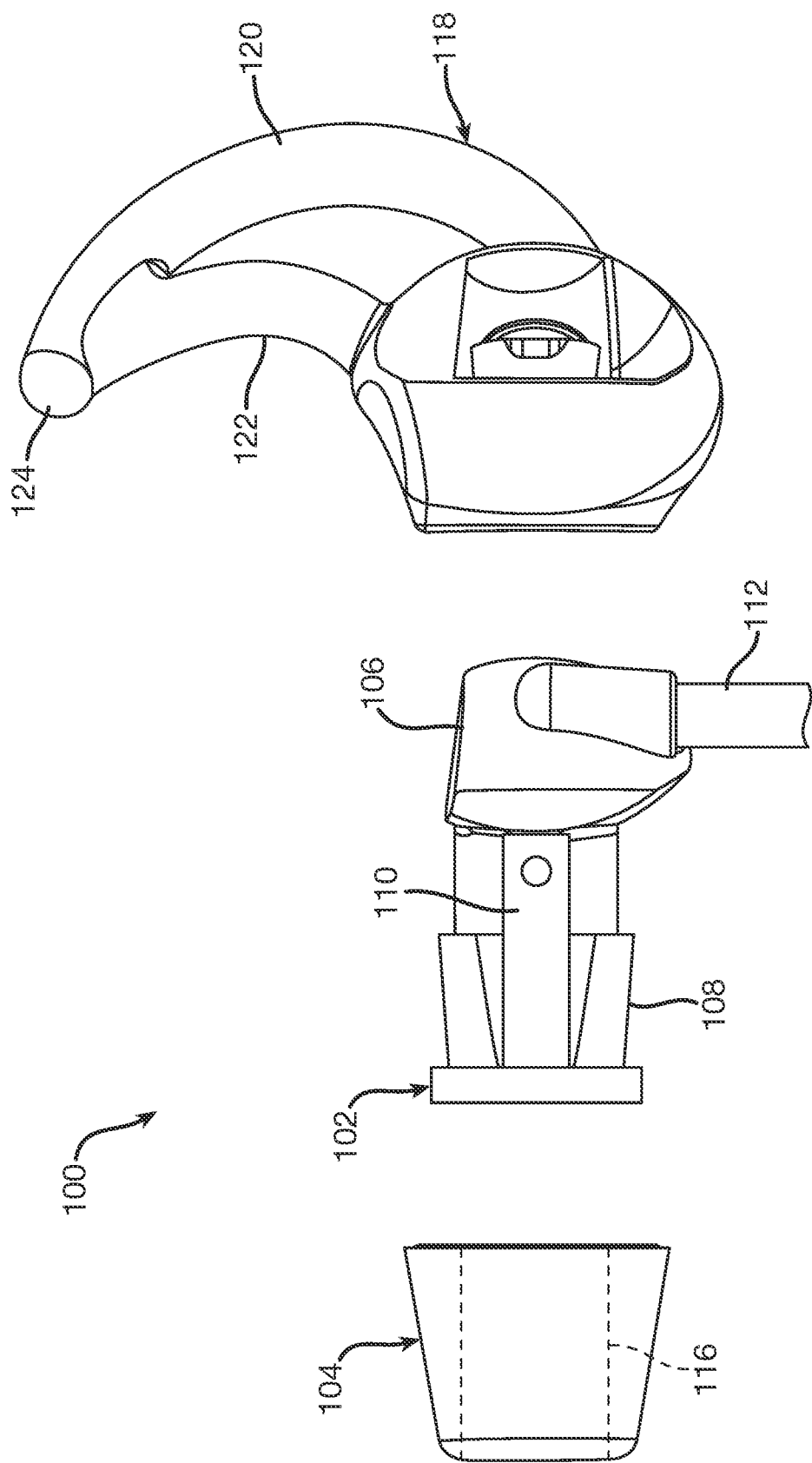
FIG. 1D is an exploded rear view of the earpiece of FIG. 1A.

It is noted that the drawings of the various implementations are not necessarily to scale. The drawings are intended to depict only typical aspects of the disclosure, and therefore should not be considered as limiting the scope of the implementations. In the drawings, like numbering represents like elements between the drawings.

DETAILED DESCRIPTION

Vagus nerve stimulation (VNS) is a medical treatment that involves delivering electrical impulses to the vagus nerve, which can be via an ear canal or in the region of an ear. It has been used as a treatment for depression, insomnia, and tinnitus. In some cases, metal electrodes are placed in contact with a surface on a person's ear and current is delivered to the electrodes to administer the therapy.

The present disclosure relates to an earpiece capable of delivering a therapeutic electrical stimulation to a user's vagus nerve via the user's ear. The present disclosure is based, at least in part, on the realization that it may be desirable to distribute the current so that there is no localized buildup of charge, which may occur if the person's skin is in direct contact with a metal electrode. That is, when a metal electrode is placed in direct contact with a person's skin certain areas of the metal electrode may make better contact than other areas so all the current would be localized in that space, which can potentially burn or damage the skin. So, the idea is to dissipate that charge by improving the contact. Hydrogels are one way that we can potentially do that.

With reference to FIGS. 1A through 1D, an exemplary earpiece 100 for delivering VNS therapy includes an earbud 102 and an ear tip 104. The earbud 102 includes a rigid housing 106 that defines a nozzle 108 which supports a pair of electrodes 110. The housing 106 may be formed of, e.g., molded from, a hard plastic such as Acrylonitrile Butadiene Styrene (ABS), Polycarbonate/Acrylonitrile Butadiene Styrene (PCB/ABS), polyetherimide (PEI), or stereolithography (SLA) resin. Wiring 112 extends into the housing 106 and couples to the electrodes 110 for providing an electrical current to the electrodes 110. In some cases, an electro-acoustic transducer 114 (FIG. 1C) may be supported in the housing 106. The electro-acoustic transducer 114 may be acoustically coupled to an acoustic passage in the nozzle 108 such that the electro-acoustic transducer 114 can be acoustically coupled to a user's ear canal when the earpiece is worn. The electro-acoustic transducer 114 can be used to deliver audio content, e.g., entertainment audio, such as music, or therapeutic audio such as guided meditation or guided breathing. In some cases, a VNS treatment, applied via the electrodes 110, is coordinated with guided breathing audio, such as described in U.S. patent application Ser. No. 16/567,116, titled "SYSTEMS AND METHODS FOR PROVIDING AND COORDINATING VAGUS NERVE STIMULATION WITH AUDIO THERAPY," filed Sep. 11, 2019 and incorporated herein by reference.

The ear tip 104 is in the shape of hollow cylinder with a hollow passage 116 that is configured to receive the nozzle 108 of the earbud 102 such that the ear tip 104 overlies the electrodes 110. Notably, the ear tip 104 may be formed of, e.g., molded from, a hydrogel. The ear tip 104 is configured to be received within a user's ear canal and such that the hydrogel is disposed between the user's skin and the electrodes 110. The hydrogel is a compliant material that can conform to the user's ear geometry to help ensure a tight fit, and good, distributed contact with the user's ear canal. The hydrogel is hydrated with an electrically conductive liquid to provide an electrically conductive path between the electrodes and the user's skin A suitable hydrogel is Poly(N-isopropylacrylamide), poly(NIPAM) or PNIPAM for short. PNIPAM is desirable because it tends to release liquid that it is hydrated with at body temperature. When heated above 32° C., the PNIPAM undergoes a reversible lower critical solution temperature phase transition from a swollen state to a dehydrated state, losing ~90% of its volume. This can help to ensure that good electrical contact is established between the user's ear and the electrodes 110, and that the electrical contact at the surface of the user's skin is distributed over the outer surface of the ear tip 104. This distributed electrical contact can help to inhibit localized application of current.

As mentioned above, the hydrogel is hydrated with an electrically conductive liquid. Suitable liquids for this purpose include salt water, deionized water, tap water, ionic liquids, and electrolytes in water for example, NaCl, CaCl, KCl. The purpose of the liquid is to wet the surface of the hydrogel to create a barrier between the ear tip 104 and the user's skin. By having the whole ear tip 104 made of the hydrogel, it will spread out the charge such that it goes from one electrode (anode) passes through the hydrogel to the user's body and then routing back to the other electrode (cathode) through the hydrogel.

Hydrogels can tend to be weak and can tear easily. To help alleviate this weakness and provide a more robust ear tip 104, strengthening additives may be added to the hydrogel when the ear tip 104 is formed. Suitable strengthening additives include cellulose nanocrystals (CNCs). In some cases, the hydrogel includes 1% % to 10%, e.g., 4% to 6%, by weight of cellulose nanocrystals. Furthermore, the introduction of liquid to hydrate the hydrogel can also contribute to the growth of mold, particularly if the ear tip 104 is packaged for distribution in a hydrated state. To inhibit mold growth an anti-microbial additive may be added to the hydrogel during formation of the ear tip 104. A suitable anti-microbial additive is silver phosphate glass. In some cases, the hydrogel includes 0.1% to 1% by weight of anti-microbial additive (e.g., silver phosphate glass).

Alternatively, or additionally, the ear tip 104 may be formed of a rubber blended with an ionic liquid.

As shown in FIGS. 1A through 1D, the earpiece 100 may also include a positioning and retaining structure 118. The positioning and retaining structure 118 can help to keep the earpiece 100 seated in the user's ear. As shown in the illustrated example, the positioning and retaining structure 118 may be formed separately from the ear tip 104 and is configured to be coupled (e.g., releasably coupled) to the earbud 102. The positioning and retaining structure 118 includes an outer leg 120 and an inner leg 122. The outer leg 120 is curved to generally follow the curve of the anti-helix (FIG. 12) at the rear of the concha of the subject's ear. Distal ends of the legs 120, 122 are joined at a point 124. The position and retaining structure 118 may be formed of, e.g., molded from a compliant material such as silicone, polyurethane, thermoplastic elastomer (TPE), and/or fluoroelastomer.

In some implementations, the housing 106 may carry one or more first electrodes on the nozzle 108 and one or more second electrodes that underlie the positioning and retaining structure 118. For example, the one or more second electrodes may underlie a portion of the positioning and retaining structure that receives the housing 106. In such cases, the positioning and retaining structure may be formed of a hydrogel that is hydrated with an electrically conductive liquid, such as described above, for helping to establish good electrical contact between the one or more second electrodes and a user's ear.

Figure 2:
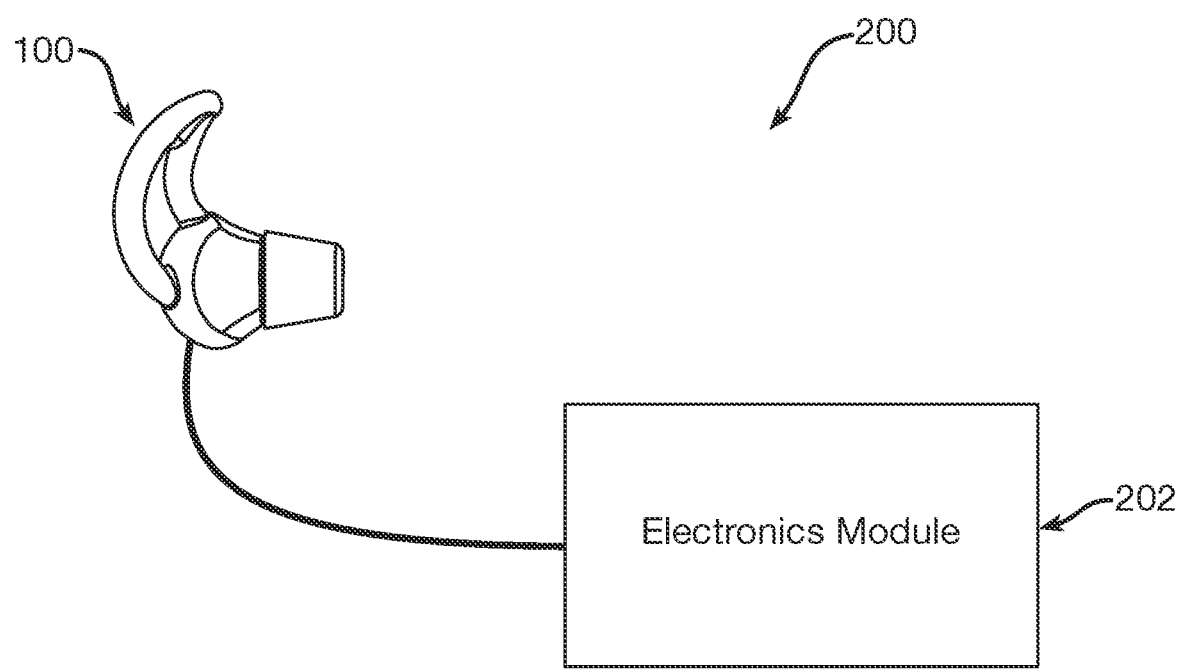
FIG. 2 is a schematic view of a vagus nerve stimulation (VNS) system including the earpiece of FIG. 1A.

As shown in FIG. 2, the earpiece 100 may be incorporated into a vagus nerve stimulation (VNS) system 200. The system 200 includes the earpiece 100 and an electronics module 202, which is coupled to the earpiece 100 via the wiring 112. The electronics module 202 houses the electronics for powering the earpiece 100. The electronics module 202 includes the programming for providing a current waveform, e.g., a bi-phasic waveform, to the electrodes 110 for VNS treatment. The electronics module 202 may also include a user interface, e.g., hardware buttons or a graphical user interface, to all the user or a clinician to adjust settings.

Figure 3:
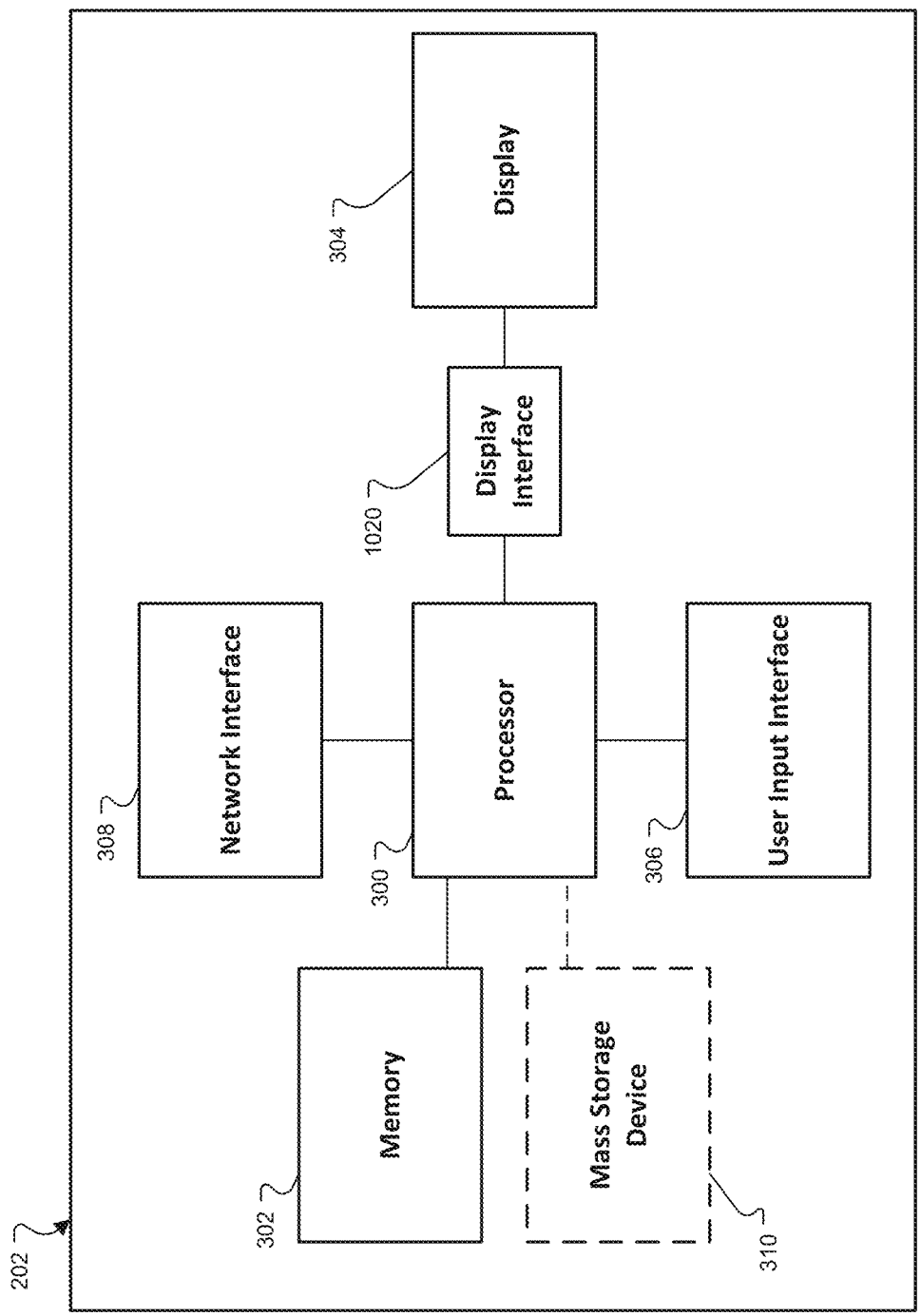
FIG. 3 is a schematic view of an electronics module from the VNS system of FIG. 2.

Referring to FIG. 3, an exemplary electronics module 202 includes a processor 300, a memory 302, a display 304, a user input interface 306, and a network interface 308, among other components. The electronics module 202 may also be provided with a mass storage device 310, such as a hard drive, a micro-drive, or other device, to provide additional storage. Each of the processor 300, the memory 302, the display 304, and the network interface 308 are interconnected using various buses, and several of the components may be mounted on a common motherboard or in other manners as appropriate.

The processor 300 can execute instructions (e.g., software) within the electronics module 202, including instructions stored in the memory 302 or in a secondary storage device (e.g., mass storage device 310). The processor 300 may be implemented as a chipset of chips that include separate and multiple analog and digital processors. The processor 300 may provide, for example, for coordination of other components of the electronics module 202, such as control of user interfaces, applications run by the electronics module 202, and network communication by the electronics module 202. The processor 300 may communication with a user through the display 304 and the user input interface 306.

The processor 300 may communicate with the user through a display interface 312 coupled to the display 304. The display 304 may include an LCD monitor, or a touch sensitive display (e.g., in the case of a mobile device). The display interface 312 may comprise appropriate circuitry for driving the display 304 to preset graphical and other information to the user.

The user input interface 306 may include one or more user input devices such as a keyboard, a pointer device such as a mouse, and/or a touch sensitive display. In some cases, the same device (e.g., a touch sensitive display) may be utilized to provide the functions of the display 304 and the user input interface 306.

The memory 302 stores information within the electronics module 202. In some implementations, the memory 302 is a volatile memory unit or units. In some implementations, the memory 302 is a non-volatile memory unit or units. The memory 302 may also be another form of computer-readable medium, such as magnetic or optical disk.

The mass storage device 310 can provide mass storage for the electronics module 202. In some implementations, the mass storage device 310 may be or contain a computer readable medium, such as a floppy disk device, a hard disk device, an optical disk device, or a tape device, a flash memory or other similar solid state memory device, or an array of devices.

Instructions (e.g., software) can be stored in an information carrier. The instructions, when executed by one or more processing devices (e.g., the processor 300), perform one or more processes, such as generating current waveforms for VNS therapy. The instructions can also be stored by one or more storage devices such as computer- or machine-readable mediums (for example, the memory 302, the storage device 310, or memory in the processor 300).

While Poly(N-isopropylacrylamide) hydrogel has been described, other hydrogels may be used. Other suitable hydrogels include Poly vinyl alcohol (PVA), crosslinked gelatin, Poly acrylic acid (PAA), and Poly ethylene glycol (PEG).

Figure 4:
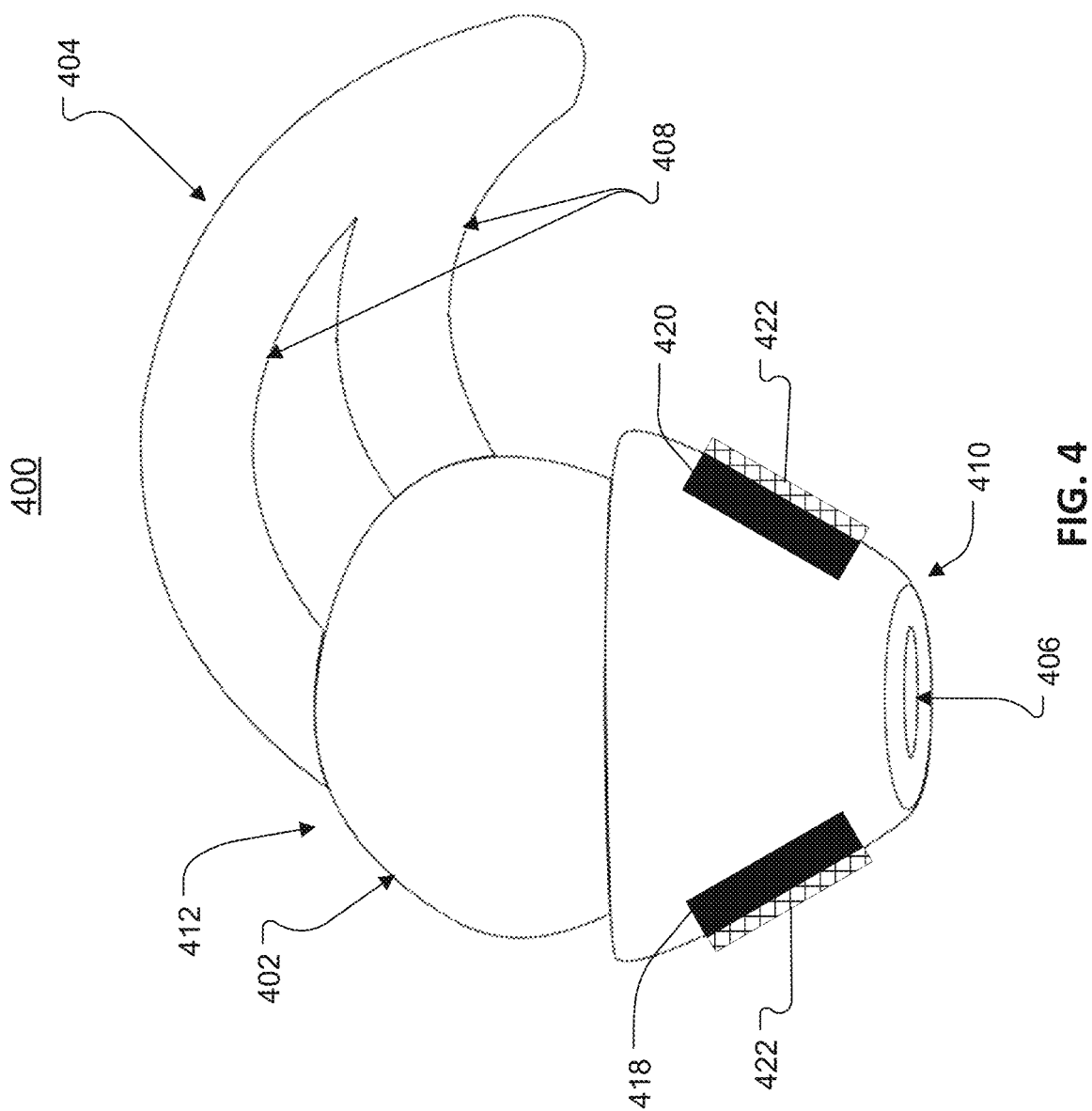
FIG. 4 is an example view of an ear tip.
Figure 5:
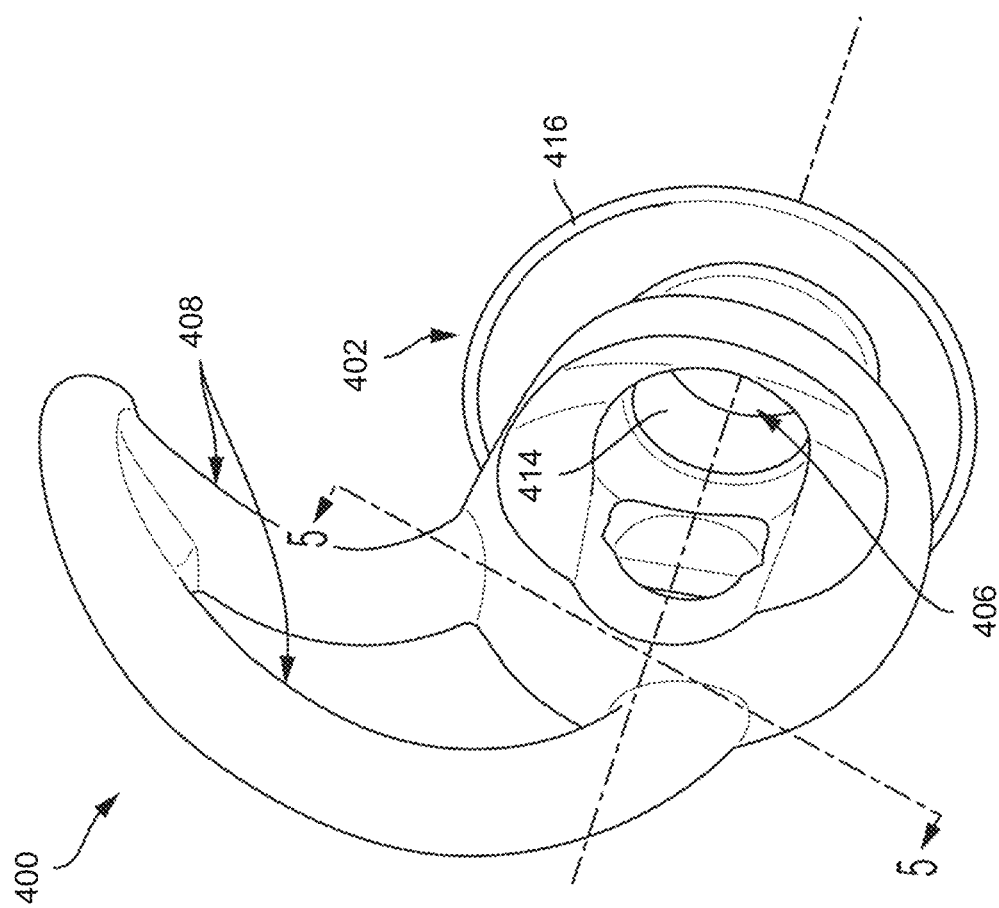
FIG. 5 is a partial cross-sectional view of an example ear tip.

FIG. 4 shows another example ear tip 400 that is configured to fit at least partially into a person's ear canal. The ear tip 400 includes a body 402 that is configured receive and/or be mounted onto an earbud (such as the earbud 102 described above with respect to FIGS. 1A-1D) and an integral retaining structure 404 that is configured to hold the ear tip in place when worn. FIG. 5 is a partial cross-sectional view of ear tip 400. The following should be viewed in light of FIGS. 4-5. The ear tip 400 can include body 402, and hollow passage 406, and retaining legs 408. Although FIGS. 4-5 show retaining legs 408 as one embodiment of the retaining structure 404, this disclosure is not limited to such a configuration. Any type of retaining structure is contemplated. Alternatively, the retaining structure 404 can be omitted altogether. The retaining legs 408 are optional.

The body 402 includes first end 410 and second end 412 opposite the first end 410. The second end 412 is proximate to the retaining legs 408. The body 402 further includes inner wall 414 extending between the first end 410 and the second end 412. Inner wall 414 defines and surrounds hollow passage 406 which can be configured to conduct sound waves. The body 402 also includes outer wall 416 connected to the inner wall 414 at the first end 410. Outer wall 416 tapers away from the inner wall 414 toward the second end 412. In example aspects, outer wall 416 is frustoconical in shape. As shown in FIGS. 4-5, the outer wall 416 tapers toward the second end 412 but does not necessarily reach the second end 412. In alternate embodiments not shown, outer wall 416 could extend to the second end 412 or beyond second end 412. Body 402 can be made of any suitable soft, flexible materials, including, for example, silicone, polyurethane, polynorbornene (e.g., Norsorex® material available from D-NOV GmbH of Vienna, Austria), thermoplastic elastomer (TPE), and/or fluoroelastomer.

The ear tip 400 includes electrically conductive elements 418, 420, which are positioned to contact skin within the ear. Although FIG. 4 shows one particular configuration of an ear tip with electrically conductive elements 418, 420 arranged on opposite sides of an outer surface of outer wall 416 (configured to fit at least partially into a person's ear canal), this disclosure is not limited to such a configuration, and any number of electrically conductive elements can be placed in any configuration on ear tip 400 as long as the electrically conductive elements are arranged to contact skin within the ear when the earpiece is worn by a user, e.g., for delivering a current to stimulate a user's vagus nerve. The electrically conductive elements 418, 420 are also configured to establish an electrical connection to electrodes on an earbud that is received within the body 402 of the ear tip 400. Electrical connections between the electrically conductive elements 418, 420 and the electrodes on an earbud received within the body 402 of the ear tip 400 may be established in a number of ways, e.g., as discussed below with respect to FIGS. 6-9. Examples of electrically conductive elements include a metal pad, metal button, metal foils (e.g., gold, silver), metal-salt hybrids (e.g., silver/silver-chloride), polymeric composites (e.g., rubbers compounded with conductive fillers such as carbon black, carbon nanotubes, graphene, silver, glass-coated silver), intrinsically conductive polymers (e.g., poly(3,4-ethylenedioxythiophene) polystyrene sulfonate or PEDOT:PSS), and/or conductive fabric (e.g., fabrics with conductive yarns, fabrics coated with conductive materials). Preferably, the electrically conductive elements are made of soft, flexible materials. The electrically conductive elements can be incorporated on to the ear tip using an ink and applying it using screen printing, pad printing, or in-mold decorating. Alternatively, the conductive elements can be incorporated wholly on to the ear tip via injection, transfer or compression molding.

Notably, a cover layer 422 is provided over the electrically conductive elements 418, 420 and is arranged such that the cover layer 422 is disposed between the conductive elements 418, 420 and a user's skin when the earpiece is worn. In some cases, the cover layer 422 may be a coating of hydrogel, such as Poly(N-isopropylacrylamide). The hydrogel may be hydrated with an electrically conductive liquid, e.g., saltwater, to help ensure a good electrical connection is established between the user's ear and the underlying conductive elements. As mentioned above, the hydrogel also helps to ensure that the electrical connection between the conductive elements and the user's skin is distributed so that the risk of a localized electrical connection is reduced.

Alternatively, or additionally, the coating 422 may comprise an ionomer. Suitable ionomers include a sulfonated tetrafluoroethylene based fluoropolymer-copolymer (Chemical formula $C_7HF_{13}O_5S.C_2F_4$) sold under the brand name Nafion by DuPont de Nemours, Inc. of Wilmington Del.; sulfonated poly(styrene-b-isobutylene-b-styrene) (S-SIBS); and sulfonated polystyrene-b-poly(ethylene-r-butylene)-b-polystyrene (S-SEBS). These materials are interesting in that they are hygroscopic in that they want to absorb a lot of moisture. These materials help to wick moisture from the skin to provide the distributed electrically conductive pathway between the underlying conductive elements and the user's skin. These ionomers do not have the weak mechanical problems that poly-NIPAM has. S-SIBS is elastomeric and Nafion is more like a plastic, so it is relatively robust. The idea is that the ionomer layer would wick relatively quickly to hydrate. These materials are interesting in that they are ionic conductors, replacing the need for ionic conducting gels in traditional wet electrode applications. They are also biocompatible and antimicrobial, which is beneficial for on-body applications. Crosslinked versions of S-SIBS and S-SEBS may also be used. These would have superior sebum resistance for on-body applications.

In some cases, the coating 422 may be formed on the conductive elements via a chemical vapor deposition processes, e.g., a hygroscopic polymer layer may be deposited on the surface of the conductive elements. The chemical vapor deposition may be used to create a coating that includes a plurality of microstructure, e.g., micropillars, which can help to increase the available surface area for establishing an electrical connection. The polymer deposited via the chemical vapor deposition process may be an electrically conductive polymer.

Figure 6:
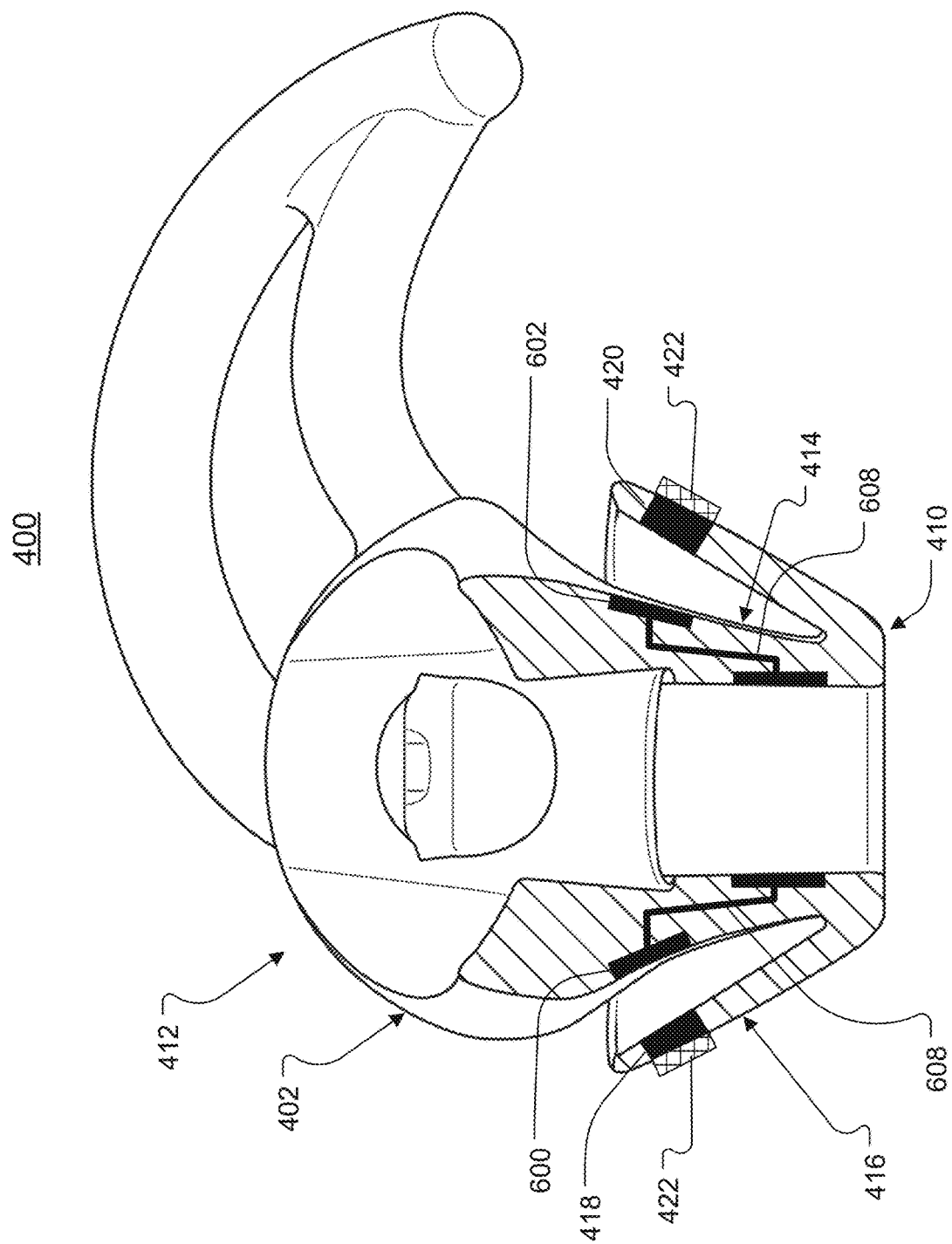
FIG. 6 illustrates an example configuration of the ear tip shown in FIG. 5, shown in a cross-sectional view generally along line 5-5 in FIG. 5.

FIG. 6 illustrates a configuration of the ear tip 400 having first and second electrically conductive elements 418, 420 arranged on an outer surface of deformable outer wall 416. The conductive elements 418, 420 can be created, for example, by punching holes in the deformable outer wall 416 and filing the holes with silver/silver-chloride (Ag/AgCl). In FIG. 6, the inner wall 414 includes first and second conductive leads 600, 602 (e.g., metal-plated pads, such as gold-plated discs) that are configured to electrically connect with the first and second electrically conductive elements 418, 420 when outer wall 416 is deformed toward inner wall 414 as ear tip 400 is placed in the ear of an individual. The collapsing of outer wall 416 (shown in FIG. 6 in the shape of an umbrella, or frustoconical) allows for contact of the electrically conductive elements 418, 420 with respective ones of the conductive leads 600, 602 situated behind the outer wall 416, thereby establishing and transmitting electrical signals to electronics (not shown) in the body 402 of the ear tip 400. In that regard, the conductive leads 600, 602 may be configured to be electrically coupled to electrodes supported on an earbud received within the body 402. In some cases, for example, the conductive leads 600, 602 may extend entirely through the inner wall 414 and terminate on an interior surface that overlies the electrodes carried on an earbud received within the body 402. Alternatively or additionally, an additional pair of conductive leads 604, 606 may be provided on an interior surface of the inner wall 414, for contacting the electrodes on the earbud, and a conductive trace, wire or via (represented generally at 608) may couple the conductive leads 600, 602 on the exterior surface of the inner wall 414 to respective ones of the conductive leads 604, 606 on the inner surface of the inner wall 414 such that, when the outer wall 416 is deformed toward the inner wall 414 the electrodes on the earbud are placed in electrical communication with the user's skin via the various conductors on the ear tip 400.

Figure 7:
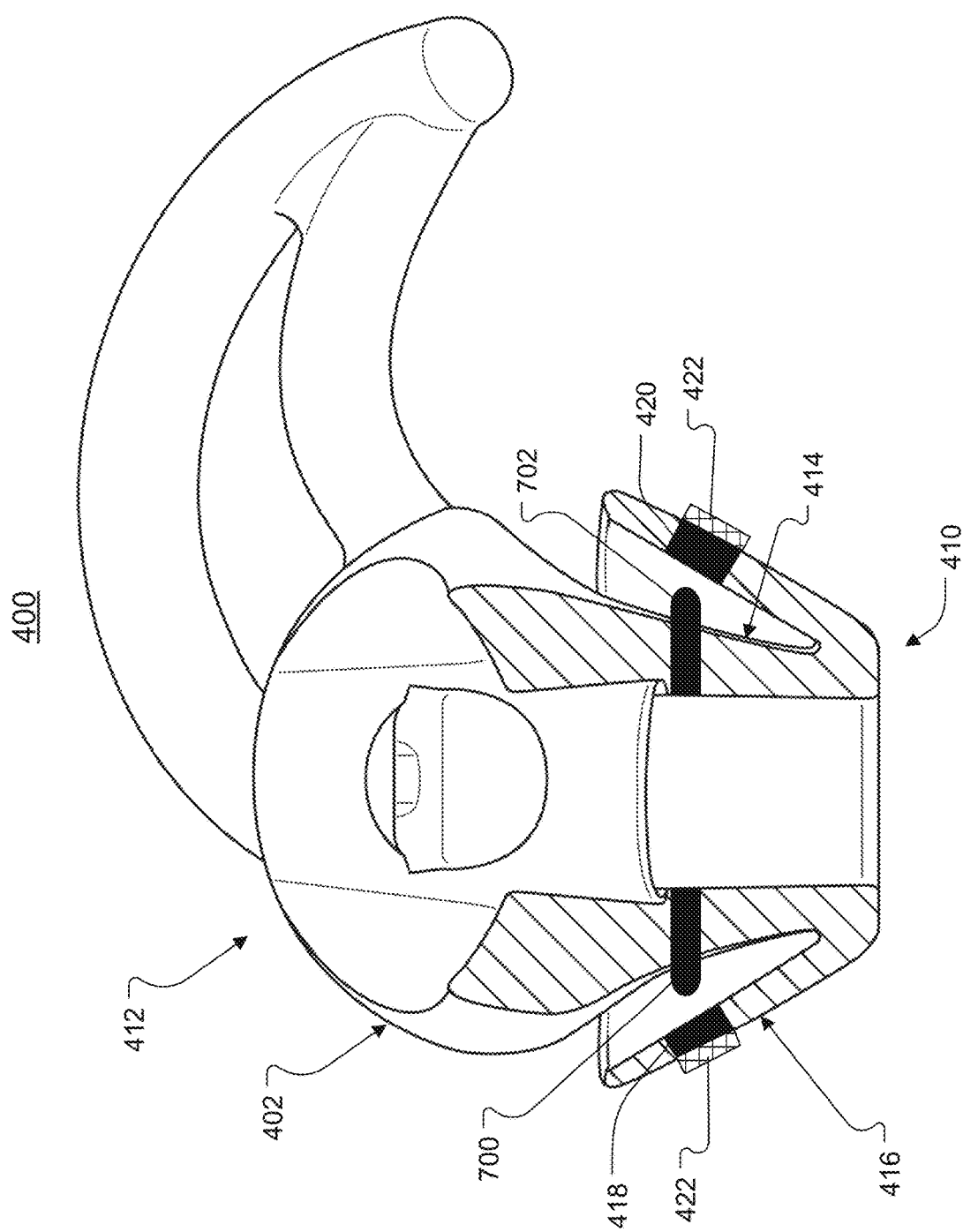
FIG. 7 illustrates another example configuration of the ear tip shown in FIG. 5, shown in a cross-sectional view generally along line 5-5 in FIG. 5.

FIG. 7 illustrates another configuration of the ear tip 400 having first and second electrically conductive elements 418, 420 arranged on an outer surface of the deformable outer wall 416. In FIG. 7, inner wall 414 includes first and second conductive pins 700, 702 (e.g., pogo pins or spring loaded connectors) that are configured to electrically connect with first and second electrically conductive elements 418, 420 when outer wall 416 is deformed toward inner wall 414 as ear tip 400 is placed in the ear of an individual. The collapsing of outer wall 416 (shown in FIG. 7 in the shape of an umbrella, or frustoconical) allows for contact of electrically conductive elements 418, 420 with respective conductive pins 700, 702 situated behind deformable outer wall 416, thereby establishing and transmitting electrical signals to electronics (not shown) in body 402 of the ear tip 400. Optionally, angled through-holes may be created in the deformable outer wall 416 such that the conductive pins 700, 702 align with the through-holes when the outer wall 416 is collapsed when placed in the ear. In some cases, the conductive pins 700, 702 may be supported on an earbud received within the body 402 of the ear tip 400 and serve as electrodes for delivering an electrical current to the user via the electrically conductive elements 418, 420. Conductive pins 700, 702 supported on an earbud can pass through apertures provided in the inner wall 414 so that the pins are engaged with the electrically conductive elements 418, 420 when the outer wall 416 is displaced towards the inner wall 414.

A cover layer 422 overlies the electrically conductive elements 418, 420 along the outer surface of the outer wall 416. The cover layer 422 may be a coating, such as any one of the coating described above.

Figure 8:
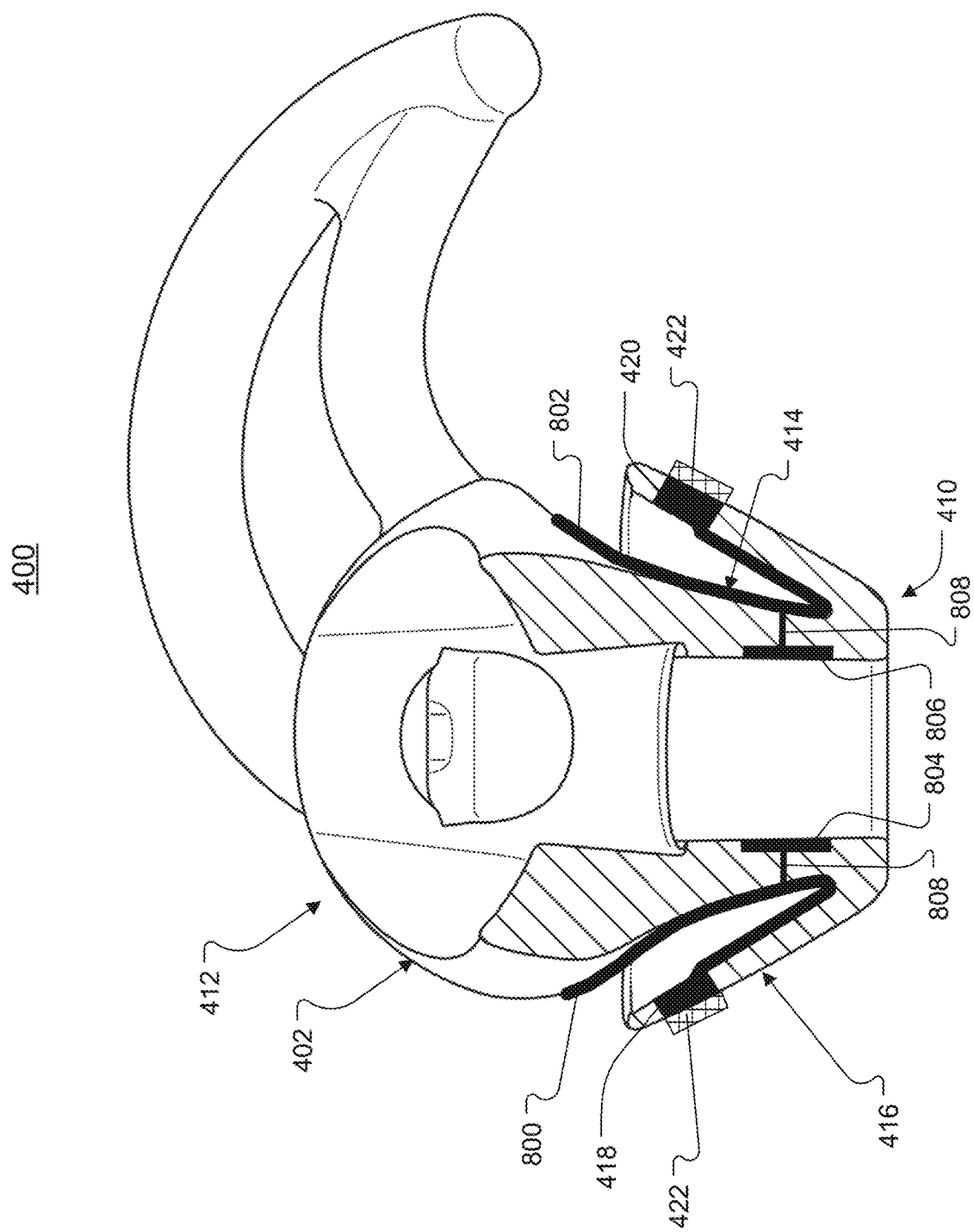
FIG. 8 illustrates another example configuration of the ear tip shown in FIG. 5, shown in a cross-sectional view generally along line 5-5 in FIG. 5.

FIG. 8 illustrates a further configuration of the ear tip 400 having first and second electrically conductive elements 418, 420 arranged on an outer surface of deformable outer wall 416. In FIG. 8, the ear tip 400 includes first and second electrical circuit elements 800, 802 (e.g., conductive fabric, such as fabric available from Eschler Textil GmbH and coated with silver/silver-chloride) connected to first and second electrically conductive elements 418, 420. The first and second electrical circuit elements 800, 802 each extend along an inner surface of deformable outer wall 416 and an outer surface of inner wall 414. The electrical circuit elements are connected to electronics (not shown) in body 402 of the ear tip 400, thereby allowing transmission of electrical signals when the ear tip 400 is placed in the ear of an individual. A pair of conductive leads 804, 806 may be provided on an interior surface of the inner wall 414, for contacting electrodes on an earbud received within the body 402. A conductive trace, wire or via (represented generally at 808) may couple the electrical circuit elements 800, 802 to respective ones of the conductive leads 804, 806 on the inner surface of the inner wall 414 such that, when the outer wall 416 is deformed toward the inner wall 414 the electrodes on the earbud are placed in electrical communication with the user's skin via the various conductors on the ear tip 400.

A cover layer 422 overlies the electrically conductive elements 418, 420 along the outer surface of the outer wall 416. The cover layer 422 may be a coating, such as any one of the coatings described above.

Figure 9:
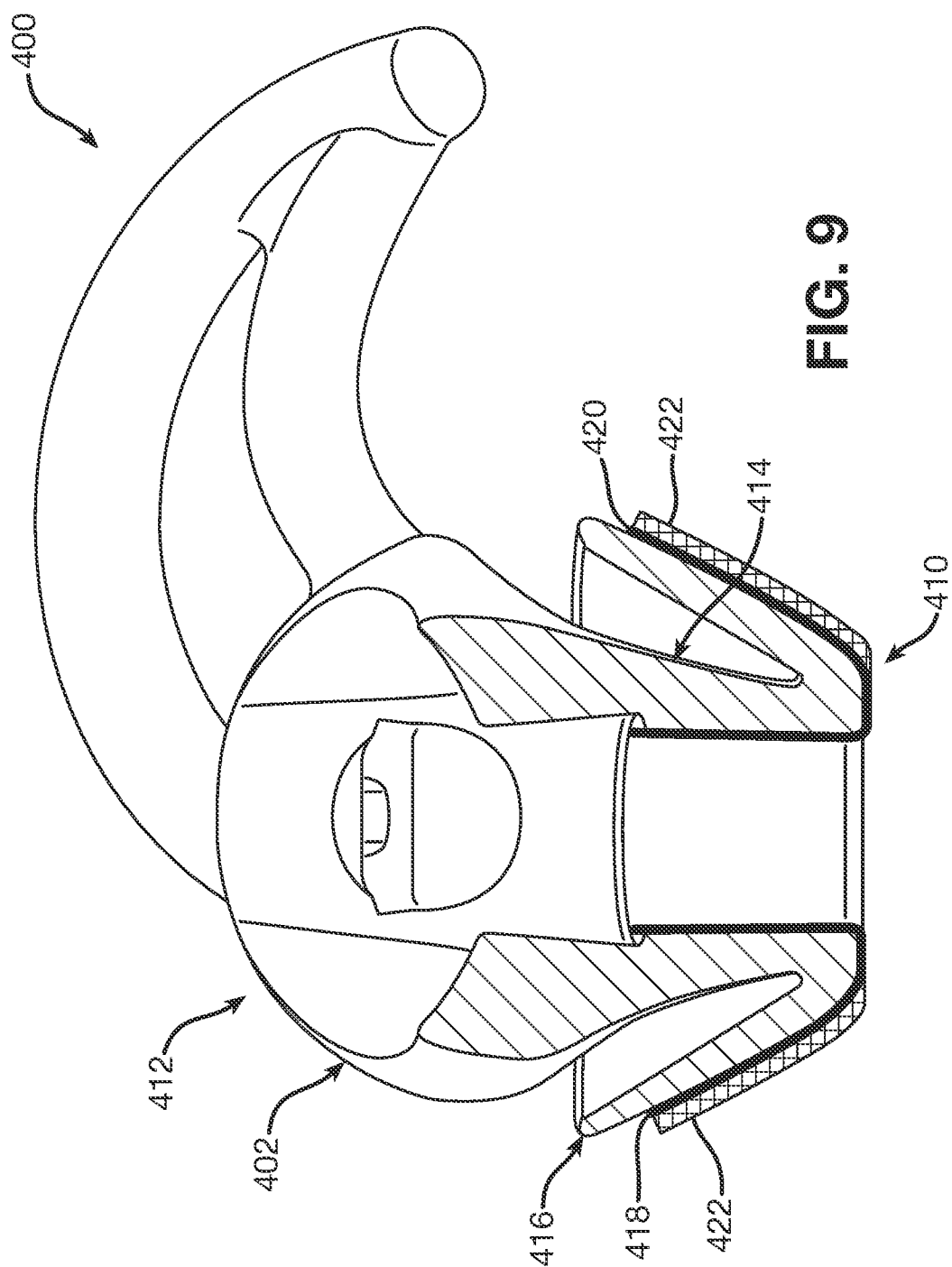
FIG. 9 illustrates another example configuration of the ear tip shown in FIG. 5, shown in a cross-sectional view generally along line 5-5 in FIG. 5.

FIG. 9 illustrates a configuration of the ear tip 400 having first and second electrically conductive elements 418, 420 (e.g., conductive fabric, such as fabric available from Eschler Textil GmbH and coated with silver/silver-chloride) each extending along an outer surface of deformable outer wall 416 and an inner surface of inner wall 414. The electrically conductive elements are connected to electronics (not shown) in body 402. In some cases, the electrical circuit elements are arranged to contact electrodes supported on an earbud received in the body 402 thereby allowing transmission of electrical signals when earpiece is placed in the ear of an individual.

A cover layer 422 overlies the electrically conductive elements 418, 420 along the outer surface of the outer wall 416. The cover layer 422 may be a coating, such as any one of the coatings described above.

Figure 10:
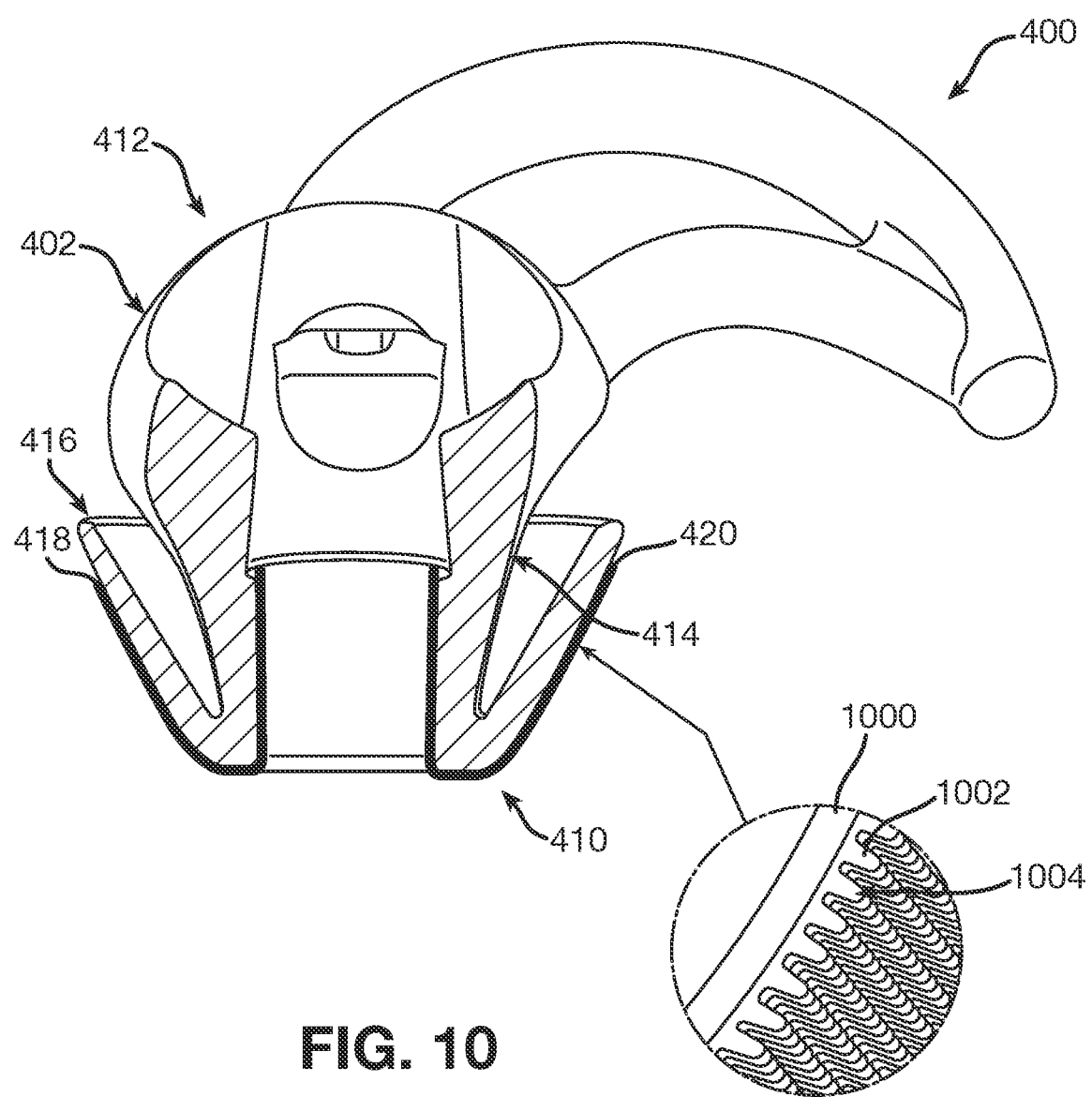
FIG. 10 illustrates another example configuration of the ear tip shown in FIG. 5, shown in a cross-sectional view generally along line 5-5 in FIG. 5.

FIG. 10 illustrates a configuration of the ear tip 400 having first and second electrically conductive elements 418, 420 each extending along an outer surface of deformable outer wall 416 and an inner surface of inner wall 414. In the example illustrated in FIG. 10, the electrically conductive elements 418, 420 are formed of a polymeric substrate 1000 having a plurality of microstructures (e.g., micropillars 1002) that extend outwardly from a surface thereof. Suitable polymeric substrates are available from the 3M Company of Maplewood, Minn., (e.g., 3M part number 300LSE) and nanoGriptech of Pittsburgh, Pa.

The surface of the substrate 1000 may be coated with silver/silver-chloride 1004 to provide electrical conductivity and/or the substrate may be formed from an intrinsically conductive polymer or a polymeric composite that includes a conductive filler such as carbon black, carbon nanotubes, graphene, silver, glass-coated silver. The electrically conductive elements 418, 420 are connected to electronics (not shown) in body 402. In some cases, the electrically conductive elements 418, 420 are arranged to contact respective electrodes supported on an earbud received in the body 402, thereby allowing transmission of electrical signals when earpiece is placed in the ear of an individual.

The micropillars 1002 may help to provide more conductive surface area to make contact with. For example, with a flat piece of conductive material there may only be contact at certain points (e.g., at localized peaks); however, the micropillar 1002 increase the number of points where contact can be established.

Figure 11:
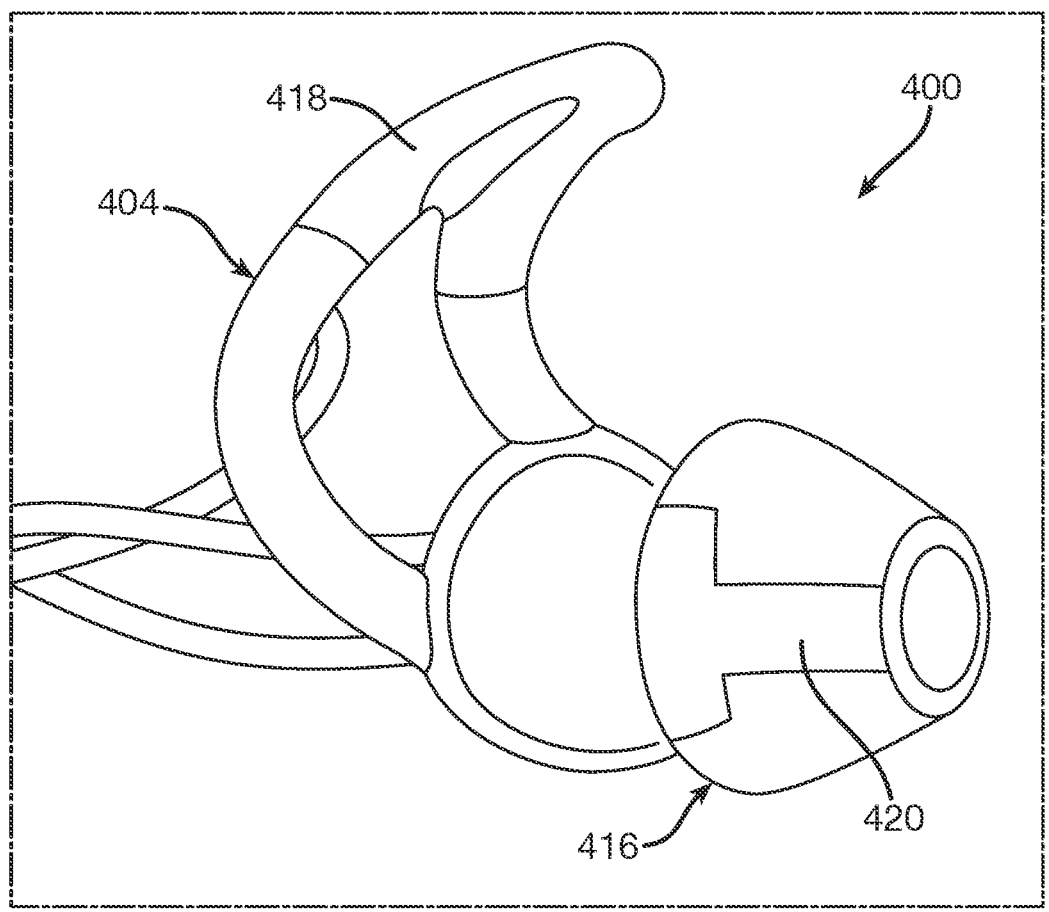
FIG. 11 illustrates another example configuration of the ear tip shown in FIG. 5.

FIG. 11 illustrates a further configuration of the ear tip 400 having a first electrically conductive element 418 arranged on the retaining structure 404 and a second ("t-shaped") electrically conductive element 420 arranged on an outer surface of deformable outer wall 416. The first electrically conductive element 418 is arranged to engage a cymba concha (FIG. 12) of a user's ear. The second electrically conductive element 420 is arranged to engage a tragus (FIG. 12) of the user's ear. A cover layer may overlie the electrically conductive elements. The cover layer may be a coating, such as any one of the coatings described above.

Figure 12:
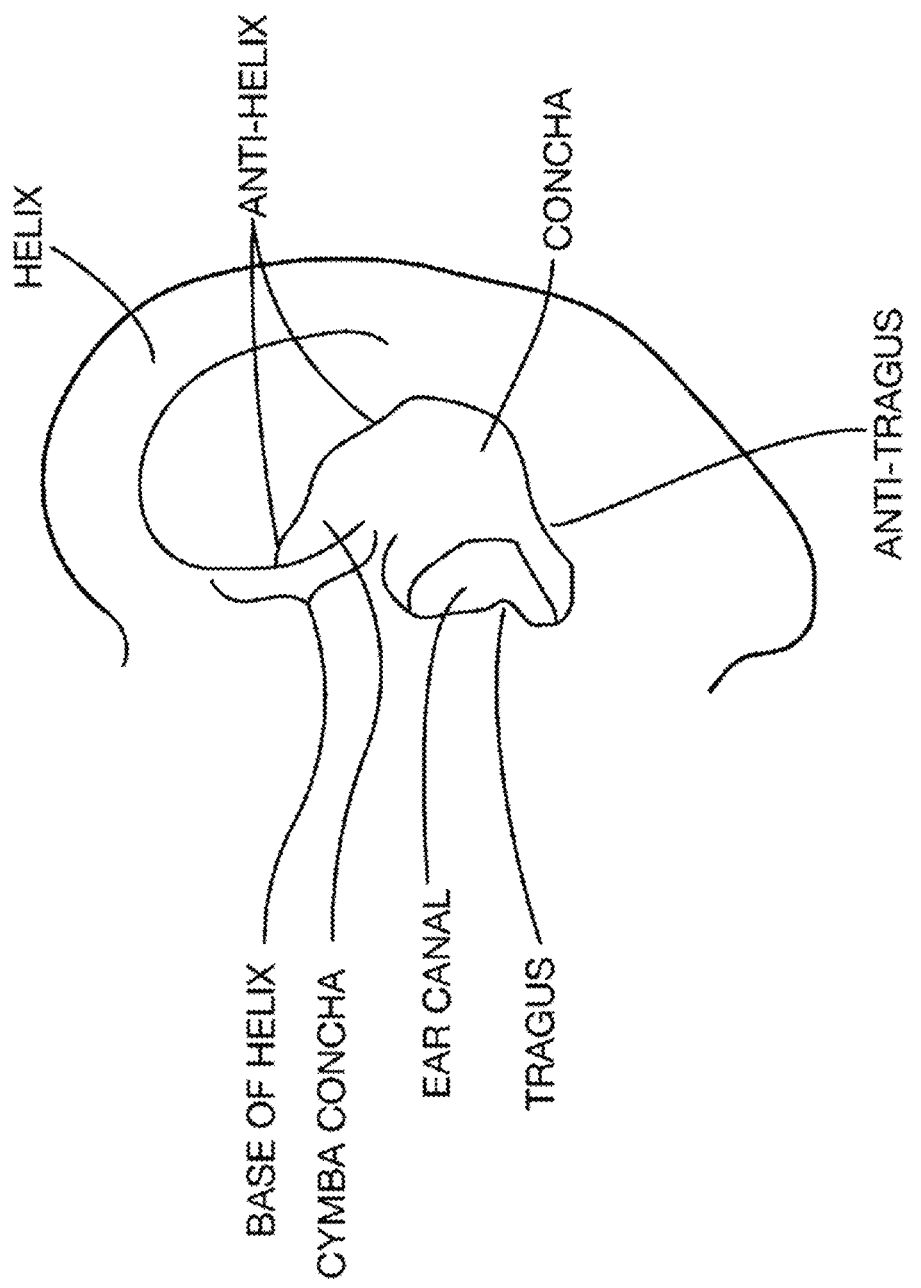
FIG. 12 is a view of the lateral surface of the human ear.

FIG. 12 shows an external portion of a human (left) ear, also known as the pinna, with some features identified. There are many different ear sizes and geometries. Some ears have additional features that are not shown in FIG. 12. Some ears lack some of the features that are shown in FIG. 12. Some features may be more or less prominent than are shown in FIG. 12.

Figure 13A:
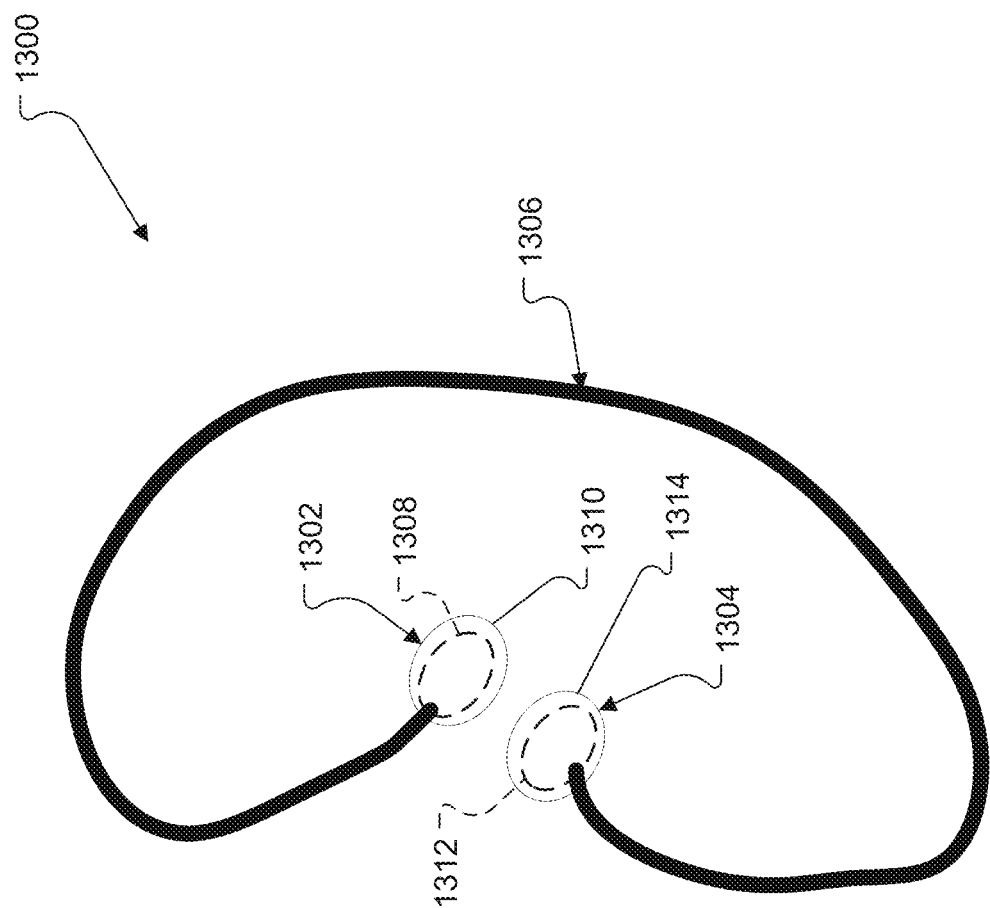
FIGS. 13A and 13B illustrate another example of an earpiece that may be used for VNS therapy.
Figure 13B:
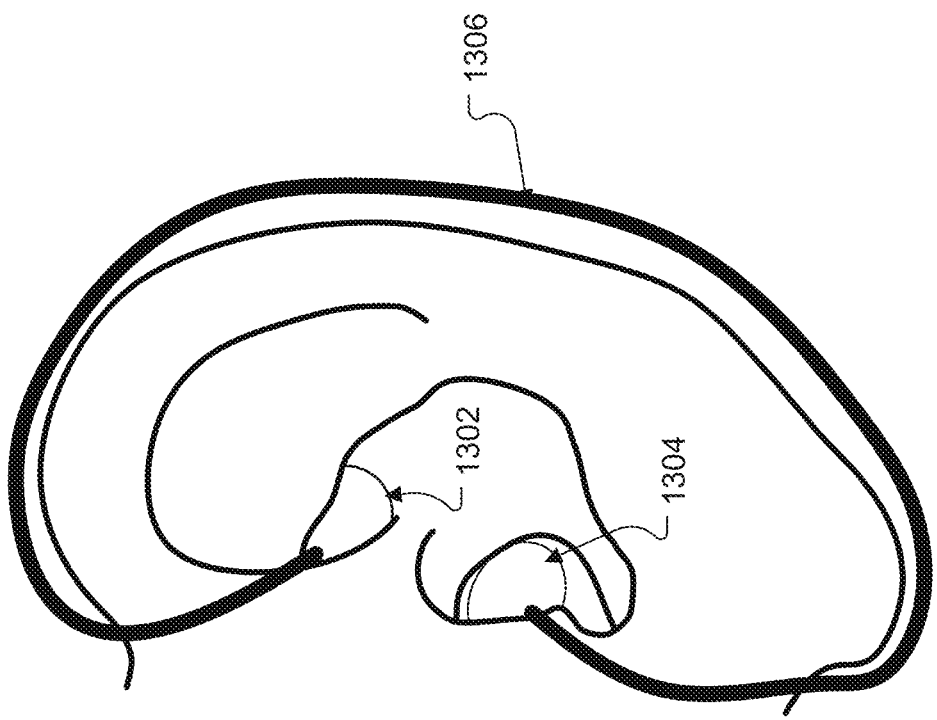

FIGS. 13A & 13B illustrates another earpiece 1300 for delivering vagus nerve stimulation therapy. The earpiece includes a pair of contacts 1302, 1304 that are mechanically coupled to each other via a coupling member 1306. A first contact 1302 is configured to rest against a cymba concha of a user's ear and includes a first electrode 1308 and a first cover layer 1310. The first cover layer 1310 overlies the first electrode 1308 such that the first cover layer 1310 is disposed between the first electrode 1308 and the user's skin when the earpiece 1300 is worn.

A second contact 1304 is configured to rest against a tragus of the user's ear and includes a second electrode 1312 and a second cover layer 1314. The second cover layer 1314 overlies the second electrode 1312 such that the second cover layer 1314 is disposed between the second electrode 1312 and the user's skin when the earpiece 1300 is worn.

The first and/or second cover layers 1310, 1314 may include a layer of hydrogel, such as Poly(N-isopropylacrylamide). The hydrogel may be hydrated with an electrically conductive liquid, e.g., saltwater, to help ensure a good electrical connection is established between the user's ear and the underlying electrodes. As mentioned above, the hydrogel also helps to ensure that the electrical connection between the electrodes and the user's skin is distributed so that the risk of a localized electrical connection is reduced. The hydrogel may be in the form of a coating applied to the surface of the electrode or as a removal tip.

Alternatively, or additionally, the first and/or second cover layers 1310, 1314 may comprise an ionomer. Suitable ionomers include a sulfonated tetrafluoroethylene based fluoropolymer-copolymer (Chemical formula $C_7HF_{13}O_5S\,C_2F_4$) sold under the brand name Nafion by DuPont de Nemours, Inc. of Wilmington Del.; sulfonated poly(styrene-b-isobutylene-b-styrene) (S-SIBS); and sulfonated polystyrene-b-poly(ethylene-r-butylene)-b-polystyrene (S-SEBS). These materials are interesting in that they are hygroscopic in that they want to absorb a lot of moisture. These materials help to wick moisture from the skin to provide the distributed electrically conductive pathway between the underlying conductive elements and the user's skin. These ionomers do not have the weak mechanical problems that poly-NIPAM has. S-SIBS is elastomeric and Nafion is more like a plastic, so it is relatively robust. The idea is that the ionomer layer would wick relatively quickly to hydrate. These materials are interesting in that they are ionic conductors, replacing the need for ionic conducting gels in traditional wet electrode applications. They are also biocompatible and antimicrobial, which is beneficial for on-body applications. Cross-linked versions of S-SIBS and S-SEBS may also be used. These would have superior sebum resistance for on-body applications.

In some cases, the cover layer 1310, 1314 may be formed on the electrodes via a chemical vapor deposition processes, e.g., a hygroscopic polymer layer may be deposited on the surface of the electrodes. The chemical vapor deposition may be used to create a coating that includes a plurality of microstructure, e.g., micropillars, which can help to increase the available surface area for establishing an electrical connection. The polymer deposited via the chemical vapor deposition process may be an electrically conductive polymer.

The coupling member 1306 mechanically couples the first and second contacts 1302, 1304. The coupling member 1306 may also carry wiring for delivering a current to the electrodes. In the example illustrated in FIGS. 13A & 13B, the coupling member 1306 is configured to wrap around the user's ear. The coupling member 1306 may be a plastic part. In some cases, the coupling member 1306 may be configured to provide a biasing force on the contacts 1302, 1304 when the earpiece 1300 is worn thereby to help keep the contacts 1302, 1304 positioned in the ear.

Figure 13C:
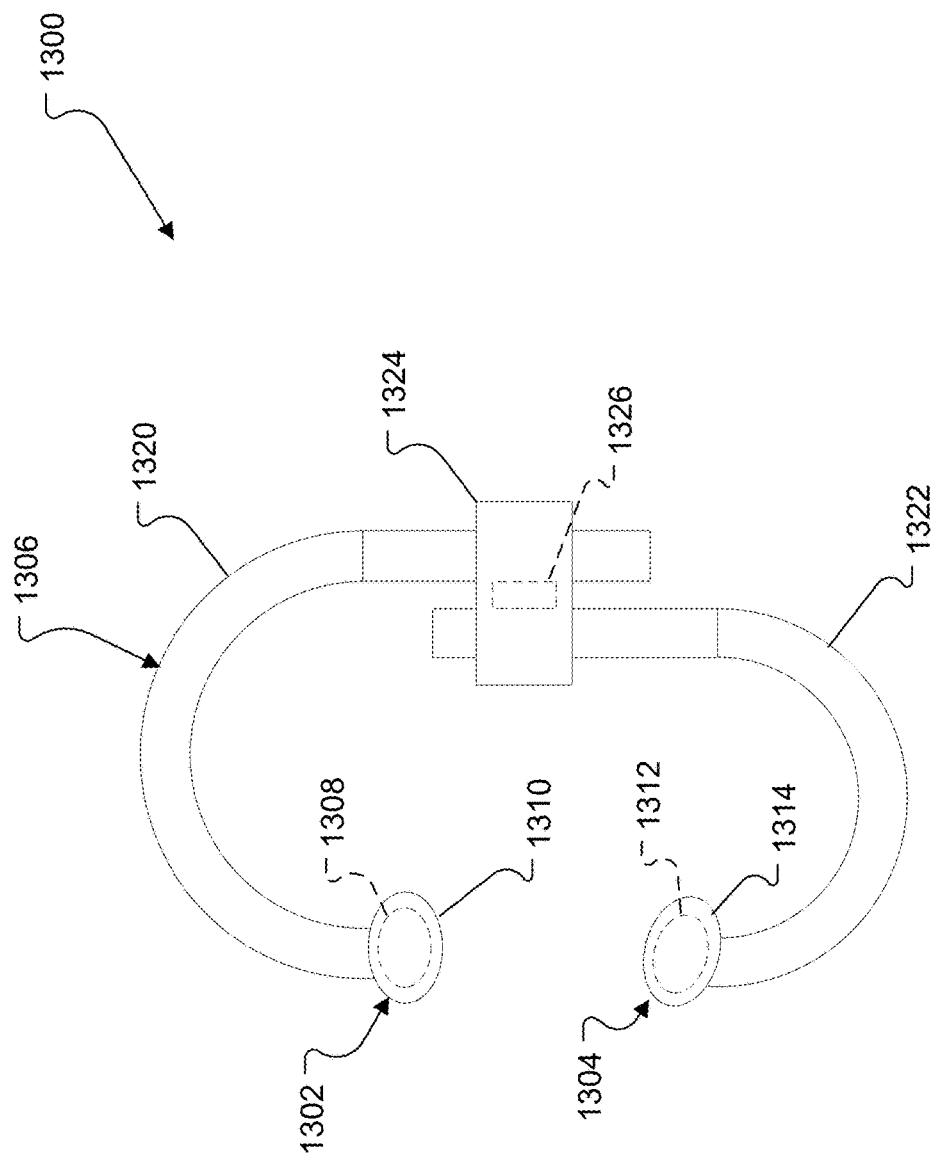
FIG. 13C is another example of an earpiece that may be used for VNS therapy.

Referring to FIG. 13C, in some implementations, the coupling member 1306 may include first and second segments 1320, 1322 that are movable relative to each other to adjust fit of the device. The first and second segments 1320, 1322 may be coupled together via a connecting member 1324. In one example, the connecting member 1324 may be formed integrally with, or otherwise mechanically fixed relative to one of the first and second segments 1320, 1322, and the other one of the first and second segments 1320, 1322 is movable relative to the connecting member 1324. In other examples, both first and second segments 1320, 1322 may be movable relative to each other and relative to the connecting member 1324.

The connecting member 1324 may include one or more through holes that receive one or more of the first and second segments 1320, 1322 with a friction fit that allows adjustment to the fit of the device. In some cases, the connecting member 1324 may support a worm gear 1326, e.g., a thumb driven worm gear, that is arranged to engage a threaded region(s) on one or both of the first and/or second segments 1320, 1322 to control displacement of the first and/or second segments 1320, 1322 relative the connecting member 1324, thereby to control fit of the device.

Figure 14A:
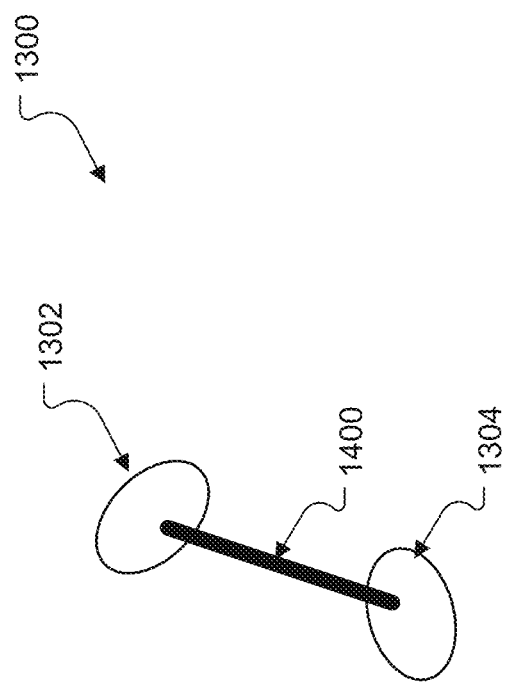
FIGS. 14A and 14B illustrate yet another example of an earpiece that may be used for VNS therapy.
Figure 14B:
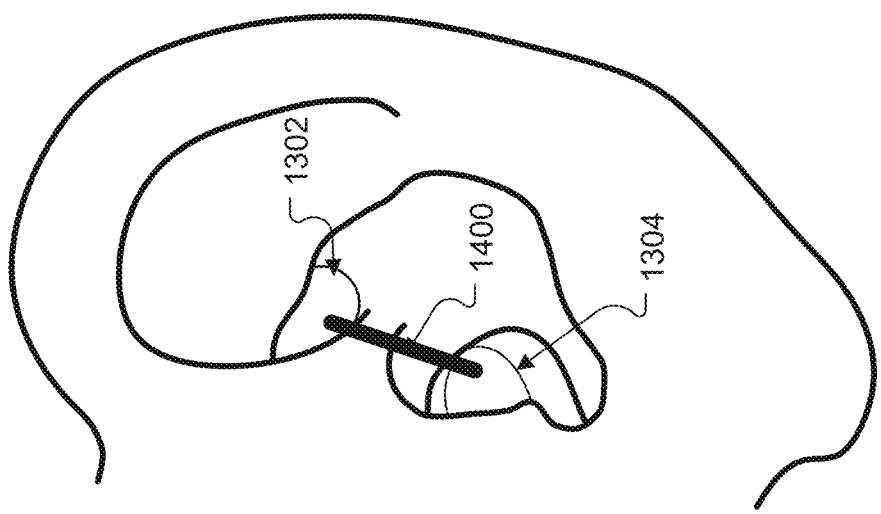

FIGS. 14A & 14B illustrate yet another configuration in which the contacts 1302, 1304 are mechanically coupled together via a coupling member 1400 that extends across the concha along a substantially straight axis across from the first contact 1302 to the second contact 1304. The coupling member 1400 may be configured to provide a biasing force to push the first contact 1302 into the user's cymba concha and to push the second contact 1304 into contact with the user's tragus when the earpiece 1300 is worn. In that regard, the coupling member 1400 may be elastically deformed during insertion and the restoring force may help to keep the earpiece in place after insertion.

As with the implementation described above with respect to FIG. 13C, the coupling member 1400 may include first and second segments, e.g., coupled together via a connecting member, that are displaceable relative to each other to control fit; i.e., to accommodate people with different ear geometries. In some cases, the segments may be axially and rotatably adjustable relative to each other.

Figure 15A:
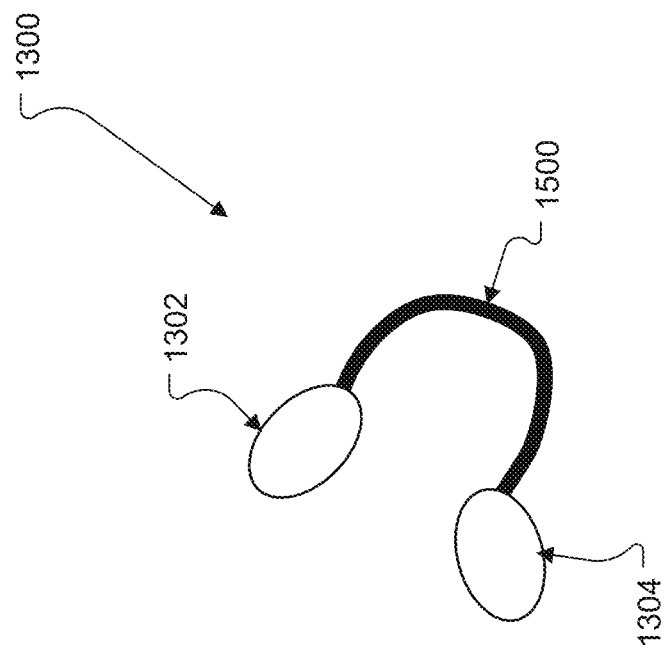
FIGS. 15A and 15B illustrate another example of an earpiece that may be used for VNS therapy.
Figure 15B:
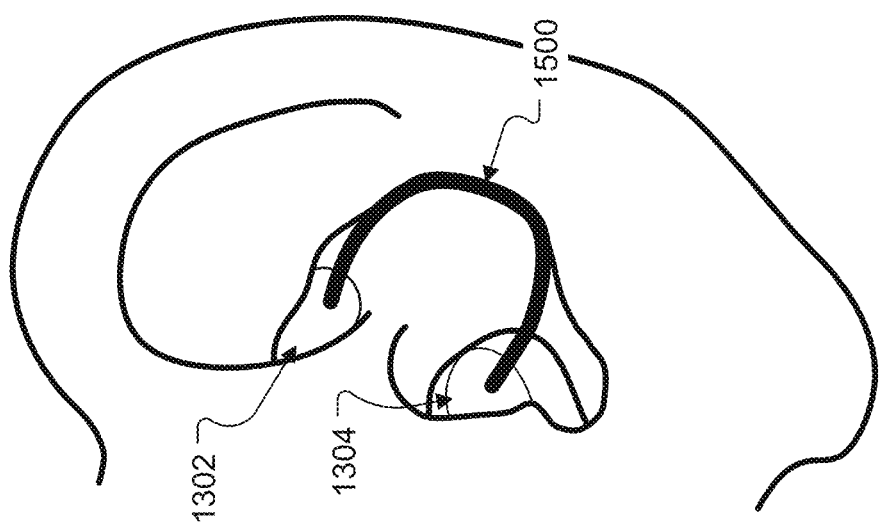

Referring to FIGS. 15A & 15B, in another configuration the contacts 1302, 1304 are mechanically coupled together via a coupling member 1500 that is configured to sit within the concha of the user's ear. The coupling member 1500 is configured to engage the anti-helix and/or anti-tragus of the user's ear to help keep the contacts 1302, 1304 engaged with the user's ear.

Figure 16:
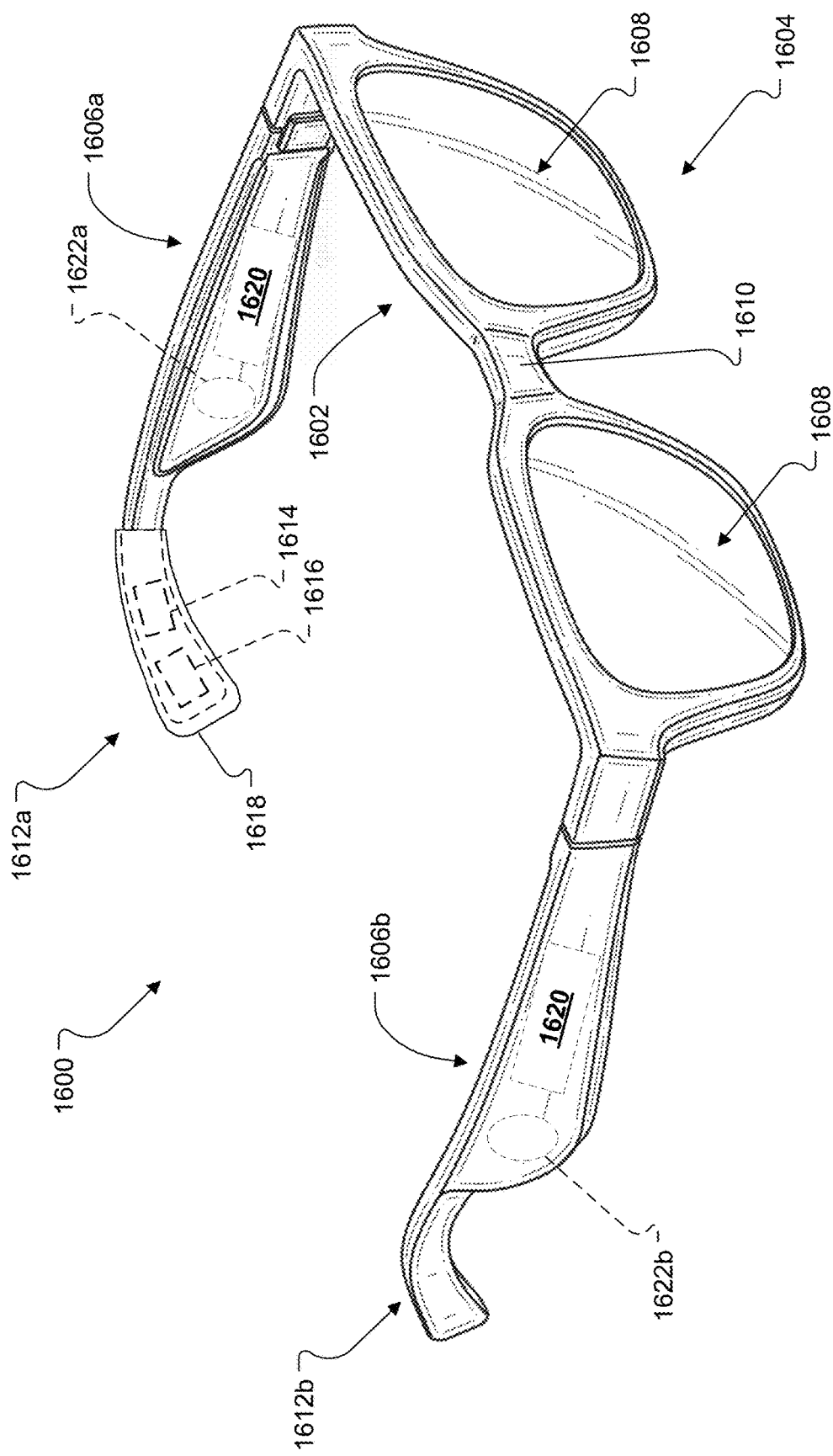
FIG. 16 is a perspective view of a set of eyeglasses as seen from the front, top, and right side.

The vagus nerve may also be accessed behind the ear. For example, FIG. 16 illustrates a pair of eyeglasses 1600 that is configured to deliver VNS therapy behind the ear of a user. The eyeglasses 1600 include a frame 1602 having a frontal region 1604 and a pair of temple pieces (also referred to as arms) 1606a and 1606b (1606, in general) extending from the frontal region 1604. As with conventional eyeglasses, the frontal region 1604 and temple pieces 1606 are designed for resting on the head of a user. The frontal region 1604 can include a set of lenses 1608 fitted to corresponding lens receptacles. The frame 1602 includes a bridge 1610 that is configured to sit on the nose.

The temple pieces 1606 are configured to sit on or near the left and right ears, typically with distal ends 1612a, 1612b (1612, in general) against the head behind the user's ear. As shown in the illustrated example, the distal end 1612a of the left temple piece 1606a includes a pair of electrodes 1614 and 1616, e.g., for applying a VNS therapy behind the user's left ear. The electrodes 1614 and 1616 may be covered with a cover layer 1618, which may be a coating, such as any of the coatings described above, or a removable tip, which may be a molded hydrogel tip that may be hydrated with an electrically conductive liquid as discussed above.

One or both temple portions 1606 may carry electronics 1620 for powering the electrodes 1614 and 1616. In some examples, the temple pieces 1606 include respective portions that each carry an electro-acoustic transducer 1622a and 1622b (1622, in general) that project sound toward an ear. The electro-acoustic transducers 1622 may also be powered by the electronics 1620. The electronics 1620 may communicate wirelessly with a computing device, such as a user's smart phone, for receiving audio content and/or data for controlling the current waveform applied via the electrodes 1614 and 1616. As mentioned above, a VNS treatment applied via the electrodes 1614 and 1616 may be coordinated with audio, e.g., guided breathing audio, provided by the electro-acoustic transducers 1622.

Figure 17:
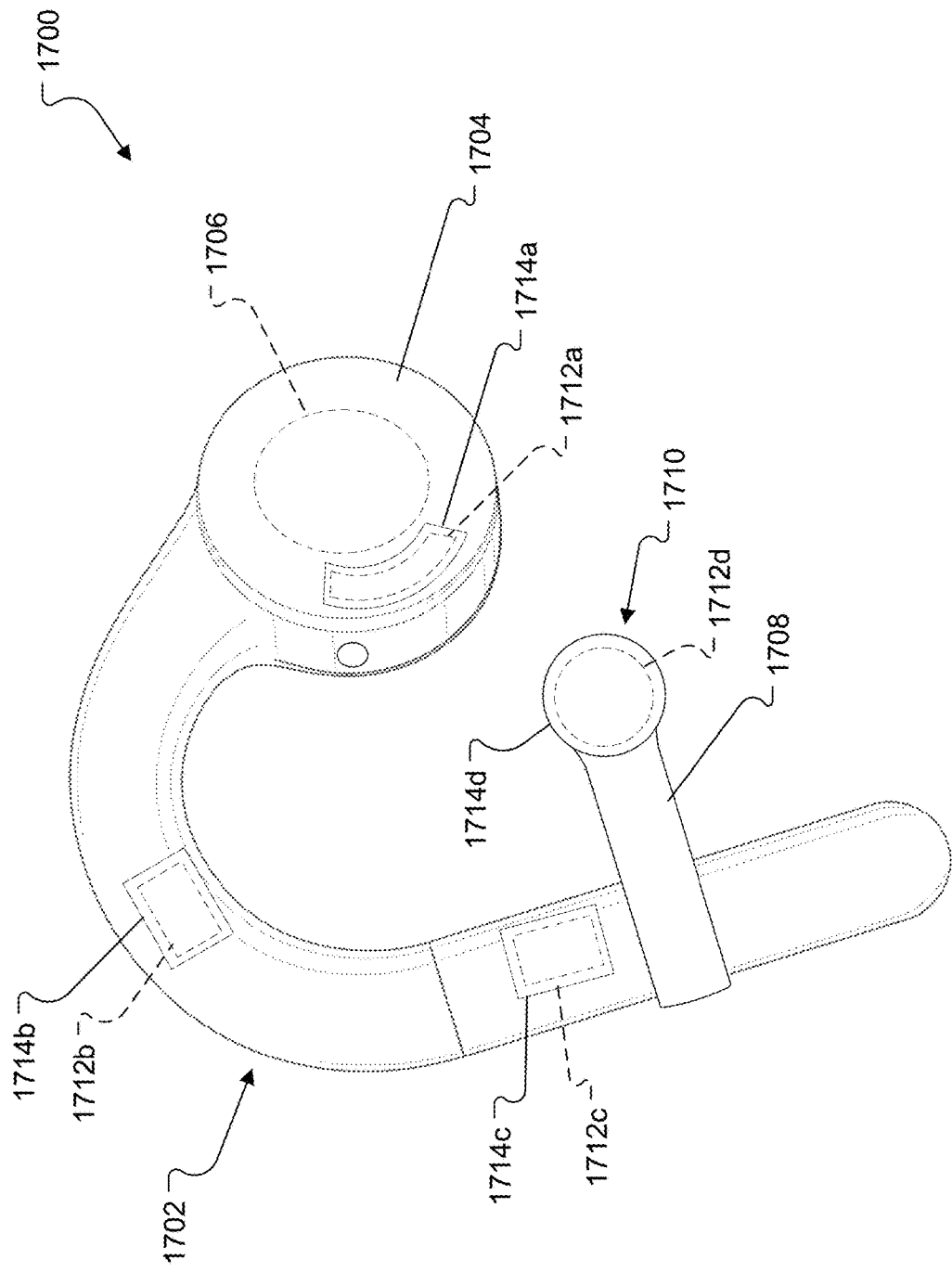
FIG. 17 is a perspective view of a headset as seen from the front, top, and right side.

FIG. 17 illustrates an example of an open audio device 1700 that is configured as an open earphone. The audio device 1700 includes an audio device body 1702 that is configured to be carried on the ear pinna and/or the head at or proximate the ear root region where the pinna meets the head. The audio device 1700 also includes portion 1704 (which may be an acoustic module) that comprises an electro-acoustic transducer 1706. The transducer 1706 delivers sound pressure from the portion 1704 directed generally toward the ear canal opening that is proximate the tragus. Open audio devices that are configured to be carried on or proximate the ear in a similar manner are disclosed in U.S. patent application Ser. No. 15/901,076 filed on Feb. 21, 2018; U.S. patent application Ser. No. 16/275,604 filed on Feb. 14, 2019; and U.S. patent application Ser. No. 16/519,220 filed on Jul. 23, 2019. The entire disclosures of these two patent applications are incorporated herein by reference.

The audio device 1700 is held on the ear and/or the head at least partially by a clamping force of the audio body 1702 on the ear and/or head. Such clamping forces are generally but not necessarily applied on generally diametrically-opposed locations of the pinna, such as near the top and bottom of the pinna. The audio device 1700 is configured to grip the ear and/or the head at these regions.

An arm 1708 is coupled to the body 1702. The arm 1708 includes a distal end 1710 that is configured to contact the ear root dimple of the user. The arm 1708 can be (but need not be) configured to be moved in two directions along the length of the body 1702, e.g., to adjust fit of the device.

As shown in FIG. 17, electrodes 1712a-d (1712, generally) may be carried on one or more of: the body 1702, the acoustic module 1704, and/or the arm 1708, e.g., for delivering VNS therapy to the user. A cover layer 1714a-d (1714, generally) may be provided over each of the electrodes 1712. The cover layer 1714 may be any of the hydrogels or ionomers discussed above.

While various devices have been described above for use with delivering an electrical signal to the ear, e.g., for VNS therapy, the electrically conductive elements may, alternatively or additionally, function as physiological electrodes for detecting bioelectrical signals of an individual, including, for example, electroencephalogram (EEG), electrooculogram (EOG), electrocardiography (ECG), and electromyogram (EMG) signals, and may also be used to detect pulse rate, respiration rate, body temperature, sweat levels, and glucose, among other health parameters. Monitoring of EEG in a wearable in-ear earpiece can be used, for example, for sleep staging, stress detection, and/or music-to-mood correlation. Monitoring of EOG in a wearable in-ear earpiece can be used, for example, for sensing movement of an individual's eyes.

A number of implementations have been described. Nevertheless, it will be understood that additional modifications may be made without departing from the scope of the inventive concepts described herein, and, accordingly, other implementations are within the scope of the following claims.

What is claimed is:

1. An earpiece comprising:
an earbud supporting first and second electrodes; and
an ear tip comprising:
- a body having:
  - first and second ends,
  - an inner wall extending between the first and second ends, and
  - a deformable outer wall connected to the inner wall at the first end and tapering away from the inner wall toward the second end;
- first and second electrically conductive elements supported by the deformable outer wall and spaced apart from each other;
- first and second conductive leads arranged on an exterior surface of the inner wall and spaced apart from each other, the first and second conductive leads being configured to electrically connect with the first and second electrically conductive elements, respectively, only when outer wall is deformed toward inner wall;
- third and fourth conductive leads arranged on an interior surface of the inner wall and configured to contact the first and second electrodes, respectively, the third and fourth conductive leads being configured to be electrically coupled to the first and second electrodes, respectively, when the ear tip is mechanically coupled to the earbud;
- first and second conductive traces extending through the inner wall coupling the first and second conductive leads to the third and fourth conductive leads, respectively; and
- a coating overlying the first and second conductive elements such that the coating is disposed between the conductive element and a user's skin when the earpiece is worn.

2. The earpiece of claim 1, wherein the coating comprises hydrogel.

3. The earpiece of claim 2, wherein the hydrogel is hydrated with an electrically conductive liquid.

4. The earpiece of claim 2, wherein the hydrogel comprises Poly(N-isopropylacrylamide).

5. The earpiece of claim 1, wherein the coating comprises an ionomer.

6. The earpiece of claim 5, wherein the ionomer comprises a hygroscopic polymer.

7. The earpiece of claim 5, wherein the ionomer is selected from the group consisting of: a sulfonated tetrafluoroethylene based fluoropolymer-copolymer; a sulfonated poly(styrene-b-isobutylene-b-styrene) (S-SIBS), and a sulfonated polystyrene-b-poly(ethylene-r-butylene)-b-polystyrene (S-SEBS).

8. The earpiece of claim 1, wherein the coating is deposited on the conductive element via chemical vapor deposition.

9. The earpiece of claim 1, wherein the coating has micropores that trap moisture.

10. The earpiece of claim 1, wherein the coating is hygroscopic.

11. The earpiece of claim 1, wherein the first and second electrically conductive elements extend through the outer wall.

12. The earpiece of claim 1, wherein the body is formed from a material selected from the group consisting of: silicone, polyurethane, polydimethylsiloxane, polynorbornene, thermoplastic elastomer, and fluoroelastomer.

* * * * *